United States Patent
Kai et al.

(10) Patent No.: US 7,038,076 B2
(45) Date of Patent: May 2, 2006

(54) FUMARATE DERIVATIVE, METHOD FOR PRODUCING THE SAME

(75) Inventors: Kazufumi Kai, Oita (JP); Keisuke Ohta, Oita (JP); Yasushi Kadowaki, Oita (JP); Hiroshi Uchida, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/088,229

(22) PCT Filed: Jul. 11, 2001

(86) PCT No.: PCT/JP01/06003

§ 371 (c)(1),
(2), (4) Date: Mar. 19, 2002

(87) PCT Pub. No.: WO02/06206

PCT Pub. Date: Jan. 24, 2002

(65) Prior Publication Data

US 2003/0060563 A1     Mar. 27, 2003

Related U.S. Application Data

(60) Provisional application No. 60/246,587, filed on Nov. 8, 2000.

(30) Foreign Application Priority Data

Jul. 19, 2000  (JP) ............... 2000-218179
Dec. 26, 2000 (JP) ............... 2000-394580

(51) Int. Cl.
*C07C 69/34*   (2006.01)
*C07C 69/52*   (2006.01)

(52) U.S. Cl. ..................... 560/198; 526/320
(58) Field of Classification Search ............... 526/320; 560/198; 425/43
See application file for complete search history.

(56) References Cited

U.S. PATENT DOCUMENTS

| | | | |
|---|---|---|---|
| 2,514,786 A | | 7/1950 | Neher et al. |
| 3,278,559 A | | 10/1966 | Reinhardt et al. |
| 4,112,146 A | * | 9/1978 | Lazear ................. 427/519 |
| 5,334,455 A | | 8/1994 | Noren et al. |
| 5,334,456 A | | 8/1994 | Noren et al. |
| 5,536,760 A | * | 7/1996 | Friedlander et al. ........ 522/96 |

FOREIGN PATENT DOCUMENTS

| | | |
|---|---|---|
| EP | 0 957 079 A1 | 11/1999 |
| GB | 1188112 | 4/1970 |
| JP | 55-39533 | 10/1980 |
| JP | 2705916 | 1/1998 |

OTHER PUBLICATIONS

"Non-Acrylate Free Radical Copolymerizable Systems For UV/EB Curing", J. J. Schouten, et al, *Rad. Tech. North America*, 1992, pp. 167-172.
International Search Report.
Johansson, M. et al, "Influence of Allyl Ethers in Coating Resins", Journal of Polymer Science: Part A: Polymer Chemistry, vol. 29, pp. 1639-1644, 1991, XP-002188713.
Klaban, Jiri et al, "Infared spectroscopic study of polymerization of bis(glycerol monoallyl ether)fumarate", Journal of Polymer Science: Part C No. 16, pp. 247-256 (1967).

* cited by examiner

*Primary Examiner*—Jeffrey B. Robertson
(74) *Attorney, Agent, or Firm*—Sughrue Mion, PLLC

(57) ABSTRACT

This invention is to provide a polymerizable composition having excellent curability and surface hardness, and a cured product thereof. A novel fumarate derivative having two or more fumarate groups within one molecule and ensuring copolymerizability with the terminal alkenyloxy group, a method for producing the derivative, a polymerizable composition containing the derivative, and a cured product thereof are provided.

3 Claims, No Drawings

FUMARATE DERIVATIVE, METHOD FOR PRODUCING THE SAME

CROSS-REFERENCE TO RELATED APPLICATIONS

This application is an application filed under 35 U.S.C. §111(a) claiming benefit pursuant to 35 U.S.C §119(e)(1) of the filing date of Provisional Application 60/246,587 filed Nov. 8, 2000 pursuant to 35 U.S.C. 111(b).

FIELD OF THE INVENTION

The present invention relates to a novel fumarate derivative having excellent radical polymerizability, capable of giving a polymer by light or heat, and usable as a crosslinking agent for various polymers, particularly usable in the field where curing in the air is required, such as coating material, coating, adhesive and sealing material, and also relates to a method for producing the derivative, a polymerizable composition containing the derivative, and a cured product thereof.

BACKGROUND OF THE INVENTION

Heretofore, polyfunctional compounds having a double bond have been used for many uses, for example, as a starting material or the like of polymerizable compositions.

These polymerizable compositions are cured predominantly by radical polymerization under light or heat. In particular, a high-speed photopolymerization by an ultraviolet ray (UV) is recently employed from the standpoint of profitability. The polymerizable composition used for the high-speed photopolymerization is generally an acrylic compound or an unsaturated carboxylic acid ester-type compound. However, these compounds have the following problems.

The acrylic compound as a crosslinked monomer can be cured within a relatively short time in UV curing and therefore, is applied to various UV curing materials such as coating material and coating, however, this monomer has a problem in that the skin irritation is relatively high and since the compound is prone to curing inhibition by oxygen, stickiness is readily generated at the formation of a thin film.

With respect to the unsaturated carboxylic acid ester-type compound, dialkyl esters of fumaric acid or maleic acid are known, however, these compounds are individually poor in the radical polymerization property and even when copolymerized with another resin, the degree of crosslinking is not sufficiently high and the cured product obtained may suffer from insufficient strength in some cases. Furthermore, the unsaturated polyester by itself has a large molecular weight and is poor in the homopolymerizability, therefore, a styrene monomer is generally used as a reactive diluent. However, in view of workability such as odor, an alternative of the styrene monomer is demanded.

In order to overcome these problems, vinyl ethers as one of alkenyl ethers are recently taken notice of as a non-acrylic compound.

The vinyl ethers are generally used as a curable material for cationic polymerization system. It is said that radical polymerization of the vinyl ether itself scarcely proceeds when used alone, however, a report in *Rad. Tech. North America,* 167 (1992) states that copolymerization proceeds between maleate and vinyl ether.

Other than this, some examples of copolymerization systems are also known. U.S. Pat. Nos. 5,334,455 and 5,334,456 describe a system where a polyfunctional vinyl ether is polymerized with a reactant between epoxy and maleic anhydride and a system where a polyfunctional vinyl ether is polymerized with a maleate, and Japanese Patent 2,705,916 describes a composition of an unsaturated polyester and a vinyl ether.

In addition, the vinyl ether is known to copolymerize with an acrylate despite its low copolymerizability.

The vinyl ether is characterized by low viscosity, excellent diluting ability and high adhesion to a substrate at the curing but, as described above, exhibits poor radical polymerizability when used alone. Therefore, in the system where an unsaturated polyester or the like is blended, the vinyl ether group is incompletely polymerized to fail in bringing out the physical properties of the cured product and furthermore, the ratio of the other polymerizable group to the vinyl ether group in the polymerization must be adjusted, giving rise to a problem that the amount of vinyl ether used is limited.

In order to overcome these problems, (the term "JP-B" as used herein means an "examined Japanese patent publication") describes a method for producing a compound having a vinyl ether group at the terminal and having a maleate structure in the inside, and British Patent 1,188,112 describes a compound having an allyl ether group at the terminal and having a maleate or fumarate structure in the inside.

These polymerizable compounds have, however, only two polymerizable groups at the terminal and one polymerizable group in the inside and still cannot have a sufficiently large number of crosslinking points.

The object of the present invention is to provide a novel fumarate derivative which can overcome the problems in conventional radical polymerizable compounds, such as curing inhibition by oxygen at curing or low surface hardness of the cured product, and which has a sufficiently large number of crosslinking points. The object of the present invention includes providing a method for producing the derivative, a polymerizable composition containing the derivative, and a cured product thereof.

DISCLOSURE OF THE INVENTION

As a result of extensive investigations to solve the above-described problems, the present inventors have found a novel fumarate derivative polyfunctionalized to have an alkenyloxy group such as vinyl ether group, propenyl ether group or allyl ether group, and a fumarate group within the same molecule and further having many double bonds. The above-described objects can be attained by using this fumarate derivative as a radical polymerizable resin or a crosslinking agent for resin. The present invention has been accomplished based on this finding.

More specifically, the present invention (I) is a fumarate derivative having at least one group represented by formula (1) as the terminal groups and having two or more groups represented by formula (2) as a repeating unit:

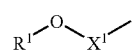

Formula (1)

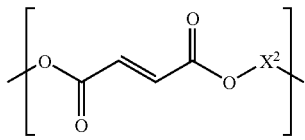
Formula (2)

(wherein in formula (1) each $R^1$ independently represents formula (3) or (4), and in formula (1) or (2), $X^1$ and $X^2$ each independently represents an organic residue derived from a polyhydric alcohol having from 2 to 6 hydroxyl groups and 2 to 30 carbon atoms, provided that $X^1$ and $X^2$ may be ester-bonded to have a branched structure having a group represented by formula (1) as the terminal groups and having a group represented by formula (2) as a repeating unit);

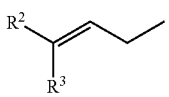
Formula (3)

(wherein $R^2$ and $R^3$ each independently represents hydrogen atom or an alkyl group having from 1 to 5 carbon atoms);
Formula (4)

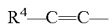

(wherein $R^4$ represents hydrogen atom or an alkyl group having from 1 to 11 carbon atoms).

And the present invention (II) is a fumarate derivative having at least one group represented by formula (1) as the terminal groups and having two or more groups represented by formula (2) and/or formula (5) as a repeating unit:

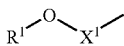
Formula (1)

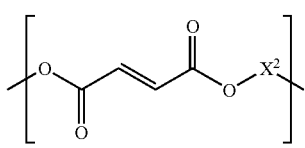
Formula (2)

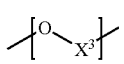
Formula (5)

(wherein in formula (1), each $R^1$ independently represents formula (3) or (4), and in formulae (1), (2) and (5), $X^1$, $X^2$ and $X^3$ each independently represents an organic residue derived from a polyhydric alcohol having from 2 to 6 hydroxyl groups and having from 2 to 30 carbon atoms, provided that $X^1$, $X^2$ and $X^3$ may be ester-bonded and/or ether-bonded to have a branched structure having a group represented by formula (1) as the terminal groups and having a group represented by formula (2) and/or formula (5) as a repeating unit);

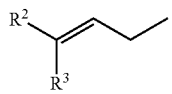
Formula (3)

(wherein $R^2$ and $R^3$ each independently represents hydrogen atom or an alkyl group having from 1 to 5 carbon atoms);
Formula (4)

(wherein $R^4$ represents hydrogen atom or an alkyl group having from 1 to 11 carbon atoms).

And the present invention (III) is a method for producing the fumarate derivative of the present invention (I) or (II).

Moreover, the present invention (IV) is a polymerizable composition comprising the fumarate derivative of the present invention (I) or (II).

And the present invention (V) is a cured product obtained by curing the polymerizable composition of the present invention (IV).

PREFERRED EMBODIMENTS OF THE INVENTION

The present invention is described below.

At first, the present invention (I) is described. The present invention (I) is a fumarate derivative having at least one group represented by formula (1) as the terminal groups and having two or more groups represented by formula (2) as a repeating unit:

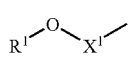
Formula (1)

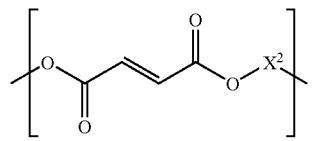
Formula (2)

(wherein in formula (1), each $R^1$ independently represents formula (3) or (4), and in formula (1) or (2), $X^1$ and $X^2$ each independently represents an organic residue derived from a polyhydric alcohol having from 2 to 6 hydroxyl groups and 2 to 30 carbon atoms, provided that $X^1$ and $X^2$ may be ester-bonded to have a branched structure having a group represented by formula (1) as the terminal groups and having a group represented by formula (2) as a repeating unit);

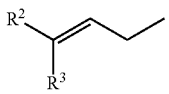

Formula (3)

(wherein $R^2$ and $R^3$ each independently represents hydrogen atom or an alkyl group having from 1 to 5 carbon atoms); Formula (4)

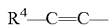

(wherein $R^4$ represents hydrogen atom or an alkyl group having from 1 to 11 carbon atoms).

The present invention (I) has at least one group represented by formula (1) in the terminal groups and containing a fumarate structure represented by formula (2) in two or more repeating unit. Representative examples thereof include a compound represented by formula (12):

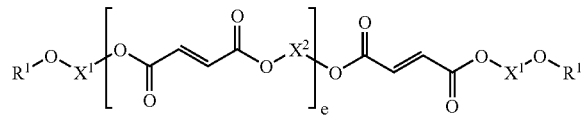

Formula (12)

(wherein e represents an integer of 1 to 9)

$R^1$ in formula (1) according to the present invention represents either formula (3) or formula (4).

In formula (3), $R^2$ and $R^3$ each independently represents hydrogen atom or an alkyl group having from 1 to 5 carbon atoms In formula (3), in view of the radical polymerizability, preferred is the case where at least one of $R^2$ and $R^3$ is hydrogen atom or a methyl group and the other is at least one of hydrogen atom, a methyl group, an ethyl group, an n-propyl group and an isopropyl group, more preferred is the case where at least one of $R^2$ and $R^3$ is hydrogen atom and the other is hydrogen atom or a methyl group, and most preferred is the case where both $R^2$ and $R^3$ are hydrogen atoms. With an alkyl group having 4 or more carbon atoms, the polymerizability may disadvantageously decrease.

In formula (4), $R^4$ represents hydrogen atom or an alkyl group having from 1 to 11 carbon atoms. In formula (4), in view of the radical polymerizability, $R^4$ is preferably at least one of hydrogen atom, a methyl group, an ethyl group, an n-propyl group and an isopropyl group, more preferably hydrogen atom or a methyl group. With an alkyl group having 4 or more carbon atoms, the polymerizability may disadvantageously decrease.

$X^1$ and $X^2$ each independently represents an organic residue derived from a polyhydric alcohol having from 2 to 6 hydroxyl groups and having from 2 to 30 carbon atoms.

Specific examples of the polyhydric alcohol include alkylene diols such as ethylene glycol, neopentyl glycol, 1,2-propylene glycol, 1,3-propylene glycol, 1,3-butanediol, 1,4-butanediol, 1,6-hexanediol and nonanediol; substituted alkylene glycols such as 1-phenylethylene glycol and 1,2-diphenylethylene glycol; and polyalkylene diols thereof; alicyclic diols such as 1,1-cyclohexanediol, 1,2-cyclohexanediol, 1,3-cyclohexanediol, 1,4-cyclohexanediol, 1,1-cyclohexanedimethanol, 1,2-cyclohexanedimethanol, 1,3-cyclohexanedimethanol, 1,4-cyclohexanedimethanol and tricyclodecanedimethanol; aromatic diols such as bisphenol A, bisphenol F, bisphenol S and benzenedimethanol; and ethylene oxide adducts, propylene oxide adducts, cyclohexene oxide adducts and styrene oxide adducts of the above polyhydric alcohol.

Also, trihydric alcohols such as trimethylolethane, trimethylolpropane and glycerol; tetrahydric alcohols such as pentaerythritol, diglycerol and ditrimethylolpropane; hexahydric alcohols such as dipentaerythritol and sorbitol; and ethylene oxide adducts, propylene oxide adducts, cyclohexene oxide adducts and styrene oxide adducts of these polyhydric alcohols may be added to an extent not to cause gelation.

Moreover, depending on the kind of a polyhydric alcohol used, there exists a stereoisomer and/or a geometric isomer. For example, when $X^2$ is an organic residue derived from 1,2-cyclohexanediol, there arises the case to afford cis-cis, cis-trans or trans-trans ester bond and to be an optical isomer as a molecule. In that case, both specific optical isomers concentrated in its ratio with use of optical active column etc., and a mixture thereof without any treatment can be used.

Among these, $X^1$ is preferably an alkylene group having from 2 to 4 carbon atoms, such as ethylene group ($—(CH_2)_2—$), 1,3-propylene group ($—(CH_2)_3—$) and 1,2-propylene group ($—CH_2—CH(CH_3)—$); 1,1-cyclohexylene group, 1,2-cyclohexylene group, 1,3-cyclohexylene group, 1,4-cyclohexylene group; or a cycloalkylene having from 6 to 8 carbon atoms, such as organic residue derived from 1,1-cyclohexanedimethanol, organic residue derived from 1,2-cyclohexanedimethanol, organic residue derived from 1,3-cyclohexanedimethanol or organic residue derived from 1,4-cyclohexanedimethanol, represented by formula ($—CH_2—C_6H_{10}—CH_2—$), from the standpoint that excellent results can be obtained in view of hardness of the cured product after the polymerization.

Moreover, in order to improve the refractive index of the cured product, an alkylene diol having phenyl or phenylene group such as bisphenol A, ethylene oxide adducts of bisphenol A, 1-phenyletylene glycol and 1,2-diphenylene glycol is preferred.

The number of the repeating units of formula (2) may be two or more but is preferably from 2 to 10 (e in formula (12) is an integer of 1 to 9). If the number of repeating units exceeds 10, the viscosity excessively increases and gelation may disadvantageously occur at the time of production.

In the case where $X^1$ is an organic residue derived from a trihydric or greater polyhydric alcohol, $X^1$ may also have a branched structure represented by the following formula (13):

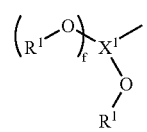

Formula (13)

(wherein f represents an integer of 0 to 4).

In the case where $X^2$ is an organic residue derived from a trihydric or greater polyhydric alcohol, $X^2$ may also have a branched structure represented by the following formula (14):

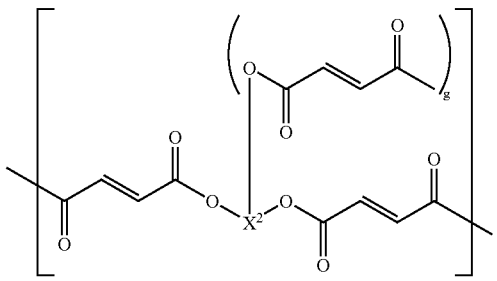

Formula (14)

(wherein g represents an integer of 0 to 4).

$R^1$ as a polymerizable group at the terminal of formula (1) is by itself poor in the radical polymerizability and curing thereof proceeds in the copolymerization with a fumarate group, therefore, when the molar ratio of $R^1$ group/fumarate group is close to 1, the cured product can have excellent physical properties. The molar ratio of $R^1$ group/fumarate group is preferably from 0.2 to 2, more preferably from 0.8 to 1.5.

$R^1$ each independently represents formula (3) or (4). Therefore, the structure of formula (3) and (4) can coexist in one fumarate derivative molecule of this invention. The terminals having the structure of formula (4) can be produced by the isomerization of all or a part of the structure of formula (3)

Next, the present invention (II) is described below. The present invention (II) is a fumarate derivative having at least one group represented by formula (1) as the terminal groups and having two or more groups represented by formula (2) and/or represented by formula (5) as a repeating unit:

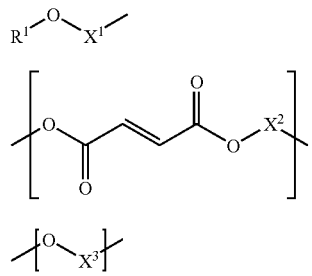

Formula (1)

Formula (2)

Formula (5)

(wherein in formula (1), each $R^1$ independently represents formula (3) or (4), and in formulae (1),(2) and (5), $X^1$, $X^2$ and $X^3$ each independently represents an organic residue derived from a polyhydric alcohol having from 2 to 6 hydroxyl groups and having from 2 to 30 carbon atoms, provided that $X^1$, $X^2$ and $X^3$ may be ester-bonded and/or ether-bonded to have a branched structure having a group represented by formula (1) as the terminal groups and having a group represented by formula (2) and/or formula (5) as a repeating unit);

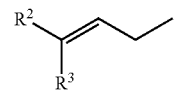

Formula (3)

(wherein $R^2$ and $R^3$ each independently represents hydrogen atom or an alkyl group having from 1 to 5 carbon atoms); Formula(4)

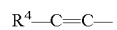

$R^4-C=C-$ (wherein $R^4$ represents hydrogen atom or an alkyl group having from 1 to 11 carbon atoms).

The fumarate derivative of the present invention (II) has at least one group represented by formula (1) as the terminal groups and contains an ether structure represented by formula (5) as a repeating structure in addition to the fumarate structure represented by formula (2).

In the present invention (II), the terminal group represented by formula (1) and the repeating structure represented by formula (2) are the same as those in the present invention (I).

$X^3$ contained in formula (5) represents an organic residue derived from a polyhydric alcohol having from 2 to 6 hydroxyl groups and having from 2 to 30 carbon atoms similarly to $X^1$ of formula (1) and $X^2$ of formula (2).

$X^3$ is also the same as $X^1$ of formula (1) and $X^2$ of formula (2) in the preferred polyhydric alcohol and in the point that $X^3$ can have a branched structure.

One representative example of the fumarate derivative of the present invention (II) is a compound represented by the following formula (15):

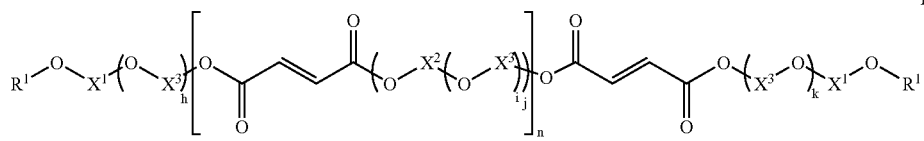

Formula (15)

(wherein h, i and k each represents an integer of 0 to 5, j represents an integer of 1 to 5 and n represents an integer of 1 to 9, provided that h+i+k≧1).

If any one of h, i, j and k exceeds 5, the concentration of the polymerizable double bond decreases to cause reduction in the curability or hardness of the cured product and this is not preferred.

The fumarate derivatives of the present invention (I) and the present invention (II) necessarily have one or more groups represented by formula (1) as a terminal group and may also partially have a carboxyl group represented by formula (8) derived from fumaric acid or a hydroxyl group derived from polyhydric alcohol, as a terminal group.

Formula (8)

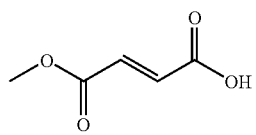

Specific examples of the fumarate derivative having a carboxyl group represented by formula (8) derived from fumaric acid as a terminal group includes a compound represented by formula (9).

Formula (9)

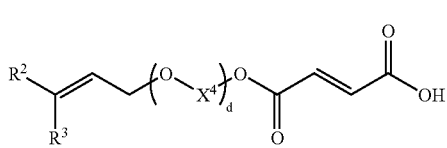

(wherein each $X^4$, which is present in the number of d in formula (9), independently represents an alkylene group or a cycloalkylene group having from 5 to 12 carbon atoms, d represents an integer of 1 to 5, and $R^2$ and $R^3$ each independently represents hydrogen atom or an alkyl group having from 1 to 5 carbon atoms).

The fumarate derivative represented by formula (9) is a polymerizable compound having an alkenyl ether group and a carboxylic acid group derived from fumaric acid as the terminal groups and having a fumarate skeleton in the inside thereof. The alkenyl ether group and the fumarate group have high radical copolymerizability. The carboxylic acid group at the terminal can form an ester bond with various hydroxyl groups and can synthesize polymerizable ester derivatives having various physical properties.

Specific examples of the compound having a hydroxyl group as a terminal group includes a compound represented by formula (10).

Formula (10)

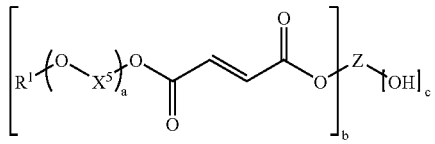

(wherein Z represents an organic residue derived from a tri-, tetra-, penta- or hexa-hydric alcohol, $R^1$ independently represents formula (3) or formula (4), each $X^5$, which is present in the number of a in formula (10), independently represents an alkylene group or a cycloalkylene group having from 5 to 12 carbon atoms, a represents an integer of 1 to 5, b represents an integer of 1 to 6, c represents an integer of 0 to 5, and b+c is from 3 to 6);

Formula (10) is a fumarate derivative preferably having either one of the allyl ether group represented by formula (3) and the propenyl ether group represented by formula (4) as a terminal group and at the same time, having a hydroxyl group derived from a polyhydric alcohol as a terminal group. In formula (10), Z represents an organic residue derived from a tri-, tetra-, penta- or hexa-hydric alcohol.

Examples of the polyhydric alcohol as used herein include trihydric alcohols such as trimethylolpropane, trimethylolethane and glycerol; tetrahydric alcohols such as pentaerythritol, ditrimethylolpropane and diglycerol; hexahydric alcohols such as sorbitol and dipentaerythritol; adducts of ethylene oxide or propylene oxide to the hydroxyl group of these tri-, tetra-, penta- and hexahydric alcohols; and mixtures of two or more thereof.

Among these, trimethylolpropane, trimethylolethane, pentaerythritol, ditrimethylolpropane, dipentaerythritol and ethylene oxide adducts of these alcohols, (in these compounds, all hydroxyl groups are primary alcohol) and mixtures of two or more thereof are preferred because of their high reactivity in the esterification reaction.

The present invention (III) is described below. The present invention (III) is a method for producing the fumarate derivative of the present invention (I) or (II).

The method for producing a fumarate derivative of the present invention (I) or (II) can be divided into the following two steps A) and B), namely, A) a step of forming an ester as the main skeleton of the fumarate derivative and forming a repeating unit of the ester, and B) a step of forming a polymerizable group at terminals represented by formula (4) by isomerization of the group represented by formula (3).

These two steps are not essential in producing the fumarate derivative of the present invention (I) or (II) and only through either one step, the fumarate derivative of the present invention (I) or (II) can be produced.

The step A) in the production method of the fumarate derivative of the present invention (I) or (II) is described below.

The fumarate derivative represented by formula (9) of the present invention (I) can be produced by a method of addition reaction of a maleic anhydride and an alcohol represented by formula (16) to obtain a maleic acid monoester and then isomerizing the ester from maleate into fumarate. In this isomerization reaction, maleate does not necessarily isomerize to fumarate by 100%, and in some cases a mixture of maleate and fumarate is obtained.

In the view point of polymerizability, the formation of fumarate is preferred.

Formula (16)

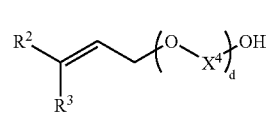

(wherein $X^4$ which exists in number of d in formula (16), each independently represents an alkylene group, a cycloalkylene group having from 5 to 12 carbon atoms or a alkylene group represented by formula (6), d represents an integer of 1 to 5, and $R^2$ and $R^3$ each independently represents hydrogen atom or an alkyl group having from 1 to 5 carbon atoms).

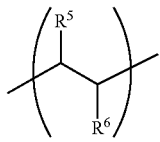

Formula (6)

(wherein $R^5$ and $R^6$ each independently represents hydrogen atom or formula (7));

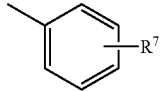

Formula (7)

(wherein $R^7$ represents hydrogen atom or an alkyl group having from 1 to 3 carbon atoms).

The fumarate derivative represented by formula (10) of the present invention (I), where $R^1$ is formula (3), can be produced by an esterification reaction of the fumarate derivative represented by formula (9) with a polyhydric alcohol.

And, the fumarate derivative represented by formula (11) of the present invention (I), where $R^1$ is formula (3), can be produced by an esterification reaction of a fumarate derivative represented by formula (9) with an alcohol represented by formula (16) or an esterification reaction of an alcohol represented by formula (16) with a fumaric acid, or a transesterification reaction between a dialkyl fumarate and an alcohol represented by formula (16).

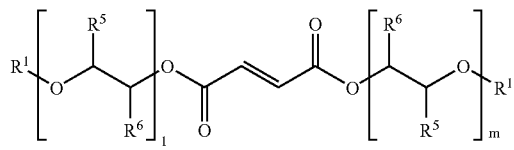

Formula (11)

(wherein, $R^1$ independently represents formula (3) or formula (4), and l and m each independently represents an integer of 1 to 5);

Furthermore, the fumarate derivative represented by formula (12) of the present invention (I), where $R^1$ is formula (3), can be produced by a transesterification reaction between a fumarate derivative represented by formula (17) and a polyhydric alcohol.

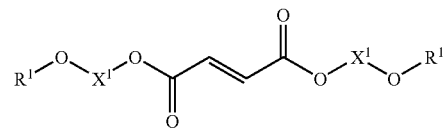

Formula (17)

(wherein each $R^1$ independently represents formula (3) or (4), and $X^1$ represents an organic residue derived from a polyhydric alcohol having from 2 to 6 hydroxyl groups and having from 2 to 30 carbon atoms).

The fumarate derivative represented by formula (15) of the present invention (II), where $R^1$ is formula (3), can be produced by a transesterification reaction between a fumarate derivative represented by formula (18) and a polyhydric alcohol represented by formula (19):

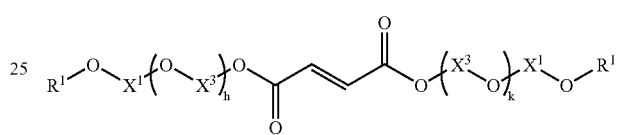

Formula (18)

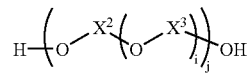

Formula (19)

And, the fumarate derivative represented by formula (20) can be produced by an esterification reaction of the fumarate derivative represented by formula (9) with an alcohol represented by formula (16) or an esterification reaction of an alcohol represented by formula (16) with a fumaric acid.

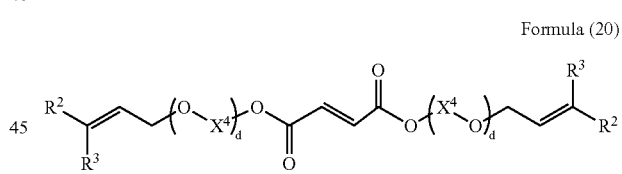

Formula (20)

(wherein $X^4$ which exists in number of d in formula (20), each independently represents an alkylene group, a cycloalkylene group having from 5 to 12 carbon atoms or a alkylene group represented by formula (6), d represents an integer of 1 to 5, and $R^2$ and $R^3$ each independently represents hydrogen atom or an alkyl group having from 1 to 5 carbon atoms).

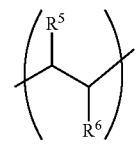

Formula (6)

(wherein $R^5$ and $R^6$ each independently represents hydrogen atom or formula (7));

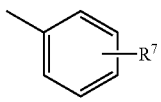

Formula (7)

(wherein $R^7$ represents hydrogen atom or an alkyl group having from 1 to 3 carbon atoms).

The method for producing the fumarate derivative represented by formula (9) is described in detail below. Specific examples of the method for producing the fumarate derivative represented by formula (9) include a method of addition reaction of a maleic anhydride and an alcohol represented by formula (16) to obtain a maleic acid monoester and then isomerizing the ester from maleate to fumarate.

The addition reaction of a maleic anhydride and an alcohol represented by formula (16) can be performed in the presence or absence of a catalyst. The catalyst is not particularly limited as long as it is a general esterification catalyst but preferred examples thereof include basic catalysts such as triethylamine and N,N-dimethylaminopyridine.

The reaction is performed at a temperature of 20 to 150° C., preferably from 40 to 120° C. If the reaction temperature is less than 20° C., the reaction proceeds slowly and unnecessarily takes a time and this is not preferred, whereas if the reaction temperature exceeds 150° C., the amount of diester produced increases and the yield disadvantageously decreases.

The ratio of the amount charged of the maleic anhydride to the amount charged of the alcohol represented by formula (16) is not particularly limited. The alcohol represented by formula (16) is generally from 0.2 to 10 equivalents in mol, preferably from 0.5 to 5 equivalents in mol, more preferably from 0.9 to 2 equivalents in mol, to 1 mol of the maleic anhydride.

If the ratio of the amount charged of the alcohol represented by formula (16) exceeds 10 equivalents in mol, excess alcohol increases, whereas if the ratio is less than 0.2 equivalents in mol, unreacted maleic anhydride increases and this is not preferred in view of profitability.

In this addition reaction, a solvent may be added. Examples of the solvent include aromatic hydrocarbons such as benzene, toluene and xylene, and ethers such as diethyl ether, dimethoxyethane, methoxy ethyl ether, tetrahydrofuran and 1,4-dioxane.

In the alcohol represented by formula (16), $R^2$ and $R^3$ each independently represents hydrogen atom or an alkyl group having from 1 to 5 carbon atoms, similarly to $R^2$ and $R^3$ in formula (3).

In the alcohol, $R^2$ and $R^3$ both are preferably hydrogen atoms in view of the polymerizability. Specific examples of the alcohol represented by formula (16) include ethylene glycol monoallyl ether, propylene glycol monoallyl ether, 1,3-butylene glycol monoallyl ether, 1,4-butylene glycol monoallyl ether, cyclohexanediol monoallyl ether, cyclohexanedimethanol monoallyl ether, diethylene glycol monoallyl ether, dipropylene glycol monoallyl ether, 2-allyloxy-2-phenylethanol, 2-allyloxy-1-phenylethanol, and 2-allyloxy-1,2-diphenylethanol.

The obtained maleic acid monoester can be isomerized into a fumaric acid monoester using a known acidic catalyst such as hydrochloric acid, a basic catalyst such as morpholine, piperidine or diethylamine, or a catalyst such as thiourea, chlorine, bromine, iodine or acid chloride.

The reaction temperature in the isomerization reaction is not particularly limited and is generally from 30 to 200° C., preferably from 50 to 150° C., more preferably from 70 to 120° C. If the reaction temperature exceeds 200° C., the polymerization or decomposition reaction disadvantageously bears higher danger.

In this isomerization reaction, a known hindered phenol-base polymerization inhibitor or a solvent may be used. Examples of the solvent used herein include aromatic hydrocarbons such as benzene, toluene and xylene; ethers such as diethyl ether, dimethoxyethane, methoxy ethyl ether, tetrahydrofuran and 1,4-dioxane; esters such as ethyl acetate and butyl acetate; ketones such as acetone and methyl ethyl ketone.

The fumarate derivative represented by formula (9) obtained as such can be purified by a treatment such as distillation, liquid separation or re-crystallization.

Next, the method for producing the fumarate derivative represented by formula (10) where $R^1$ is formula (3) is described below.

The fumarate derivative represented by formula (10) where $R^1$ is formula (3) can be produced by an esterification reaction of the fumarate derivative represented by formula (9) and a polyhydric alcohol. Specific examples of the esterification reaction include the following three methods:

① a method of esterifying the fumarate derivative represented by formula (9) and a polyhydric alcohol in the presence of an acid catalyst, ② a method of inducing the fumarate derivative represented by formula (9) into an acid halide and then reacting it with a polyhydric alcohol to perform the esterification, and ③ a method of reacting the fumarate derivative represented by formula (9) with a polyhydric alcohol using a condensing agent to perform the esterification.

The method ① is described below.

Examples of the esterification catalyst which can be used in the method ① include known catalysts such as sulfuric acid, p-toluenesulfonic acid, methanesulfonic acid, ion exchange resin, a mixed catalyst of boric acid and sulfuric acid, polyphosphoric acid and Lewis acid (e.g., boron trifluoride etherate).

The reaction can be performed under atmospheric pressure, applied pressure or reduced pressure, for example, at 15 Pa to 1 MPa in terms of an absolute pressure. The reaction temperature is from 20 to 200° C., preferably from 40 to 150° C., and the reaction is performed while distilling off water generated as a by-product. If the reaction temperature is less than 20° C., the reaction proceeds slowly, whereas if it exceeds 200° C., by-products such as polymerization product may increase.

At the reaction, a solvent may be used. The solvent used is not particularly limited and specific examples thereof include benzene, hexane, cyclohexane, toluene and xylene.

The charging ratio of the fumarate derivative represented by formula (9) to a polyhydric alcohol is not particularly limited but these are preferably charged such that the hydroxyl group (—OH) of the polyhydric alcohol is from 0.2 to 5 equivalents in mol, more preferably from 0.5 to 1.5 equivalents in mol, to the carboxyl group (—COOH) of the fumarate derivative represented by formula (9). If the charging ratio is less than 0.2 equivalents in mol, the residual amount of the fumarate derivative represented by formula (9) is excessively large, whereas if it exceeds 5 equivalents in mol, unreacted hydroxyl group disadvantageously remains.

Depending on the reaction conditions, for example, the alcohol corresponding to $R^1$—$(OX^5)_a$—OH may be partly eliminated from the ester position of the fumarate derivative represented by formula (10), this alcohol causes an esterification reaction with the carboxyl group of the fumarate derivative represented by formula (9) to produce a diester monomer of fumaric acid, and the monomer is contained in the product in some cases, however, the product can be used as a polymerizable composition without removing the monomer.

After the completion of the esterification reaction, purification may also be performed for removing the impurities or unreacted reactants. The purification may be performed, for example, by dissolving a fumarate derivative in an organic solvent such as benzene, toluene, cyclohexane, diethyl ether, methyl acetate or ethyl acetate, washing the solution with water or alkali, and thereby removing the unreacted fumarate derivative represented by formula (9) or carboxylic acids as by-product, in the form of a salt.

The purity may also be increased by a method of subjecting the product to decantation or re-precipitation with an organic solvent such as aliphatic hydrocarbons (e.g., hexane, octane), by a method of purifying the product through a column using silica gel or by thin layer chromatography.

The method ② is described below.

The method ② is a method of inducing the fumarate derivative represented by formula (9) into an acid halide and then reacting it with a polyhydric alcohol to perform the esterification.

In the method ②, the method of inducing the fumarate derivative represented by formula (9) into an acid halide is not particularly limited and a known method using thionyl chloride, phosphoryl chloride, phosphorus pentachloride, phosphorus trichloride or phosgene may be used.

Particularly, in the case where thionyl chloride is used, zinc chloride, pyridine, iodine or triethylamine may be used in combination as a catalyst. Also, a mixture of thionyl chloride and dimethylformamide, and a mixture of thionyl chloride and hexamethylphosphoric triamide are known to be a good reagent for synthesizing the acid halide.

By reacting the thus-induced acid halide of the fumarate derivative represented by formula (9) with a polyhydric alcohol using a known method, the fumarate derivative represented by formula (10) of the present invention can be produced.

The method ③ is described below.

The method ③ is a method of reacting the fumarate derivative represented by formula (9) with a polyhydric alcohol using a condensing agent to perform the esterification.

Specific examples of the condensing agent for use in the method ③ include dicyclohexylcarbodiimide, trifluoroacetic anhydride and sulfonyl chloride, however, the present invention is not limited thereto. Any commonly known condensing agent may be used without any limit.

Among these, a method of using sulfonyl chloride is preferred in view of the easiness to handle. Examples of the case where sulfonyl chloride is used as the condensing agent include a method of adding a base to the fumarate derivative represented by formula (9) in the presence of a solvent, followed by the reaction, adding sulfonyl chloride and finally adding a polyhydric alcohol, followed by the reaction.

Examples of the sulfonyl chloride used here include p-toluenesulfonyl chloride, methanesulfonyl chloride and trifluoromethanesulfonyl chloride.

The charging amounts of the fumarate derivative represented by formula (9) and the sulfonyl chloride are not particularly limited, however, sulfonyl chloride in equivalent or more is generally used. The sulfonyl chloride is preferably charged in an amount of 1 to 2 equivalents in mol to the fumarate derivative represented by formula (9).

The charging ratio of the fumarate derivative represented by formula (9) and a polyhydric alcohol is not particularly limited. These are preferably charged such that the hydroxyl group (—OH) of the polyhydric alcohol is from 0.2 to 2 equivalents in mol, more preferably from 0.4 to 1.2 equivalents in mol, to the carboxyl group (—COOH) of the fumarate derivative represented by formula (9).

The solvent used here is not particularly limited as long as it does not inhibit the reaction. Specific examples thereof include ethers such as tetrahydrofuran and dioxane; aromatic hydrocarbons such as benzene, toluene and xylene; halides such as chloroform, dichloromethane and dichloroethane; dimethylformamide; and dimethylsulfoxide.

Examples of the base include alkali metals such as sodium hydroxide, potassium hydroxide, cesium hydroxide, sodium carbonate, potassium carbonate, cesium carbonate, sodium hydrogencarbonate and potassium hydrogencarbonate.

The amount of the base varies depending on the kind thereof, however, is preferably from 1 to 5 equivalents in mol to the fumarate derivative represented by formula (9).

The reaction temperature is from −20 to 100° C., preferably from 0 to 50° C. If the reaction temperature exceeds 100° C., the side reaction increases, whereas if it is less than −20° C., the reaction may be disadvantageously delayed.

The product obtained can be purified for removing impurities. Examples of the purification method include a method of dissolving the product in an organic solvent such as benzene, toluene, xylene, cyclohexane, methyl acetate, ethyl acetate, diethyl ether, dichloroethane or chloroform, and then washing the solution with water, alkali or acid; a method of subjecting the product to decantation or re-precipitation with an organic solvent such as aliphatic hydrocarbon (e.g., hexane, octane). The purity may also be enhanced by column purification using silica gel or thin layer chromatography.

The method for producing the fumarate derivative represented by formula (11) of the present invention (I), where $R^1$ is formula (3), is described below.

The fumarate derivative represented by formula (11) of the present invention (I), where $R^1$ is formula (3), can be produced by an esterification reaction of the fumarate derivative represented by formula (9) with the alcohol represented by formula (16) or and an esterification reaction of a fumaric acid with the alcohol represented by formula (16).

Specific examples of the esterification reaction are the same with that described in the method for producing the fumarate derivative represented by formula (10) where $R^1$ is formula (3). A transesterification reaction between a dialkyl fumarate and the alcohol represented by formula (16) is exemplified as the other method.

Namely, the fumarate derivative represented by formula (11) where $R^1$ is formula (3), can be produced by reacting a dialkyl fumarate with the alcohol represented by formula (16) in the presence of known transesterification catalyst while removing alcohol generated as a by-product.

Specific examples of the dialkyl fumarate include dimethyl fumarate, diethyl fumarate, di-n-propyl fumarate, di-isopropyl fumarate, di-n-butyl fumarate, di-sec-butyl fumarate and di-t-butyl fumarate. Preferred are dimethyl fumarate, diethyl fumarate, di-n-propyl fumarate and di-isopropyl fumarate because of the easiness of removing the side-produced alcohol.

The transesterification catalyst, which can be used here, is not particularly limited. Specific examples thereof include alkali metals, alkaline earth metals, oxides thereof, oxides and hydroxides of Zn, Sn and Ti, alcoholates, and acetylacetonate complexes.

The reaction temperature is from 80 to 200° C. and the reaction may be performed under atmospheric pressure, applied pressure or reduced pressure, for example, at 15 Pa to 1 MPa in terms of the absolute pressure.

The fumarate derivative represented by formula (11) may also be obtained by once synthesizing a compound where a part of the fumarate of the fumarate derivative represented by formula (11) is maleate, and isomerizing the compound.

The maleate derivative used for this isomerization reaction can be synthesized with the same method for producing the fumarate derivative represented by formula (11) as above, namely, by an esterification reaction of a maleic acid or a maleic anhydride with the alcohol represented by formula (16).

Specific examples of the esterification reaction are the same as described in the method for producing the fumarate derivative represented by formula (10) where $R^1$ is formula (3). A transesterification reaction between a dialkyl maleate and the alcohol represented by formula (16) is exemplified as the other method.

The transesterification reaction is the same as described in the method for producing the fumarate derivative represented by formula (11) where $R^1$ is formula (3), and the maleate derivative can be produced by reacting a dialkyl maleate with the alcohol represented by formula (16) in the presence of known transesterification catalyst while removing alcohol generated as a by-product.

The catalyst for use in the isomerization reaction from maleate to fumarate is preferably a complex of an element such as palladium, rhodium or ruthenium, or a supported catalyst comprising a support having supported thereon such an element. Particularly, in the case of purifying the fumarate derivative, a supported catalyst is preferably used in view of removal of the catalyst.

The support for use in such a supported catalyst is not particularly limited and a porous substance commonly used as a catalyst may be used. Specific examples thereof include silica, alumina, silica-alumina, zeolite, activated carbon, titania, magnesia and other inorganic compounds.

The amount of the element supported on a support is preferably from 0.05 to 20% by mass, more preferably from 2 to 10% by mass, based on the entire amount of the catalyst. If the supported amount is less than 0.05% by mass, the reaction takes a time, whereas if it exceeds 20% by mass, the element not participating in the isomerization reaction disadvantageously increases.

The thus-obtained supported catalyst is preferably used in an amount of 0.01 to 50% by mass, more preferably from 1 to 30% by mass, based on the maleate derivative. If the amount used is less than 0.01% by mass, the reaction takes a time, whereas if it exceeds 50% by mass, the catalyst not participating in the isomerization reaction disadvantageously increases. The isomerization catalyst can be used individually or in combination of two or more thereof.

The temperature at the isomerization reaction is not particularly limited. The isomerization reaction temperature is generally from 30 to 200° C., preferably from 60 to 180° C., more preferably from 80 to 160° C. If the reaction temperature is less than 30° C., the reaction proceeds slowly, whereas if it exceeds 200° C., polymerization may occur during the isomerization reaction and this is not preferred.

In the present invention, the isomerization reaction may also be performed in a solvent. Examples of the solvent which can be used include aromatic hydrocarbons such as benzene, toluene and xylene; ethers such as diethyl ether, dimethoxyethane, methoxyethyl ether, tetrahydrofuran and 1,4-dioxane; esters such as ethyl acetate and butyl acetate; ketones such as acetone and methyl ethyl ketone; and alcohols such as methanol, ethanol and isopropanol. In the case of using a solvent, these solvents may be used in combination of two or more thereof.

In the present invention, the isomerization reaction may be performed under atmospheric pressure or applied pressure, for example, at a pressure of 1 KPa to 1 MPa.

During the transesterification reaction and the isomerization reaction, a polymerization inhibitor may also be added for preventing occurrence of polymerization.

Examples of the polymerization inhibitor include quinones such as p-benzoquinone, naphthoquinone and 2,5-diphenyl-p-benzoquinone; polyhydric phenols such as hydroquinone, p-tert-butylcatechol and 2,5-di-tert-butylhydroquinone; and phenols such as hydroquinone monomethyl ether, di-tert-butyl paracresol and α-naphthol.

The method for producing the fumarate derivative represented by formula (12) of the present invention (I), where $R^1$ is formula (3), is described below.

The fumarate derivative represented by formula (12) where $R^1$ is formula (3) can be produced by a transesterification reaction between the fumarate derivative represented by formula (17) and the polyhydric alcohol. Namely, the fumarate derivative represented by formula (12) where $R^1$ is formula (3), can be produced by reacting the fumarate derivative represented by formula (17) with the polyhydric alcohol in the presence of known transesterification catalyst while removing alcohol generated as a by-product.

Specific examples of the transesterification reaction are the same as described in the method for producing the fumarate derivative represented by formula (11) where $R^1$ is formula (3).

In the case of this reaction, the fumarate derivative represented by formula (17) where $R^1$ is formula (3) may remain in the product depending on the charged ratio to the polyhydric alcohol, however, the product can be used without removing it.

The fumarate derivative represented by formula (12) may also be obtained by once synthesizing a compound where a part of the fumarate of the fumarate derivative represented by formula (12) is maleate, and isomerizing the compound.

The maleate derivative used for this isomerization reaction can be synthesized with the same method for producing the fumarate derivative represented by formula (11) as above, namely, by a transesterification reaction between the maleate derivative corresponding to the fumarate derivative represented by formula (17) and the polyhydric alcohol.

The isomerization reaction from maleate to fumarate is also the same with the method for producing the fumarate derivative represented by formula (11).

The method for producing the fumarate derivative represented by formula (15) of the present invention (II), where $R^1$ is formula (3), is described below.

The fumarate derivative represented by formula (15) where $R^1$ is formula (3) can be produced by a transesterification reaction between the fumarate derivative represented by formula (18) and the polyhydric alcohol represented by formula (19).

To speak more specifically, the fumarate derivative represented by formula (18) can be produced by performing an addition reaction of an ethylene glycol allyl ether or a propylene glycol allyl ether corresponding to $R^1$—O—$X^1$—OH with an epoxy compound having the $X^3$ unit, such as ethylene oxide, propylene oxide, cyclohexene oxide or styrene oxide to synthesize a corresponding alcohol, and then an esterification reaction with a fumaric acid or a transesterification reaction with a dialkyl fumarate The polyhydric alcohol having ether-bond as represented by formula (19), for example, can be produced by an addition reaction of an alcohol such as ethylene glycol or propylene glycol with an epoxy compound such as ethylene oxide, propylene oxide, cyclohexene oxide or styrene oxide.

In the forgoing pages, the step A) of forming an ester as the main skeleton of the fumarate derivative and forming a repeating unit of the ester is described.

The step B) of forming a polymerizable group at the terminal by isomerization is described below.

The fumarate derivative represented by formula (10) of the present invention (I), where $R^1$ is formula (4) and the fumarate derivative represented by formula (11) of the present invention (I), where $R^1$ is formula (4), can be produced by a method of isomerizing the terminal group of the above-described fumarate derivative represented by formula (10), where $R^1$ is formula (3) and the fumarate derivative represented by formula (11), where $R^1$ is formula (3), respectively.

Also, the fumarate derivative represented by formula (12) of the present invention (I), where $R^1$ is formula (4) and the fumarate derivative represented by formula (15) of the present invention (II), where $R^1$ is formula (4), can be produced by isomerizing the corresponding fumarate derivatives, where $R^1$ is formula (3).

The isomerization reaction is described below.

The isomerization reaction from formula (3) to formula (4) can be performed using a known complex of an element such as palladium, rhodium or ruthenium, or using a supported catalyst comprising a support having supported thereon such an element.

The support for use in the supported catalyst is not particularly limited and a porous substance generally used as the support may be used. Specific examples thereof include silica, alumina, silica-alumina, zeolite, activated carbon, titania, magnesia and other inorganic compounds.

The amount of the element supported on a support is preferably from 0.05 to 20% by mass, more preferably from 2 to 10% by mass, based on the entire amount of the catalyst. If the amount of the element supported is less than 0.05% by mass, the reaction takes a time, whereas if it exceeds 20% by mass, the element not participating in the isomerization reaction disadvantageously increases.

The thus-obtained supported catalyst is preferably used in an amount of 0.01 to 50% by mass, more preferably from 1 to 30% by mass, based on the fumarate derivative represented by formula (10), (11), (12) or (15) containing formula (3) If the amount of the catalyst is less than 0.01% by mass, the reaction takes a time, whereas if it exceeds 50% by mass, the catalyst not participating in the isomerization reaction disadvantageously increases. The isomerization reaction catalyst may be used individually or in combination of two or more thereof.

In the isomerization reaction, the reaction temperature is not particularly limited and is generally from 30 to 200° C., preferably from 60 to 180° C., more preferably from 80 to 160° C. If the reaction temperature is less than 30° C., the reaction takes a time, whereas if it exceeds 200° C., polymerization may occur during the isomerization reaction and this is not preferred.

In the present invention, the isomerization reaction may be performed in a solvent. Examples of the solvent which can be used include aromatic hydrocarbons such as benzene, toluene and xylene; ethers such as diethyl ether, dimethoxyethane, methoxyethyl ether, tetrahydrofuran and 1,4-dioxane; esters such as ethyl acetate and butyl acetate; ketones such as acetone and methyl ethyl ketone; alcohols such as methanol, ethanol and isopropanol. In the case of using a solvent, these solvents may be used in combination of two or more thereof.

In the present invention, the isomerization reaction may be performed under atmospheric pressure or applied pressure, for example, at a pressure of 1 KPa to 1 MPa.

In order to prevent occurrence of polymerization during the isomerization reaction, a polymerization inhibitor may also be added. Examples of the polymerization inhibitor include quinones such as p-benzoquinone, naphthoquinone and 2,5-diphenyl-p-benzoquinone; polyhydric phenols such as hydroquinone, p-tert-butylcatechol and 2,5-di-tert-butylhydroquinone; and phenols such as hydroquinone monomethyl ether, di-tert-butyl paracresol and α-naphthol.

The present invention (IV) is described below.

The present invention (IV) is a polymerizable composition comprising the fumarate derivative of the present invention (I) or (II).

The polymerizable composition of the present invention (IV) may contain, if desired, a compound having radical polymerizability or a radical polymerization initiator in addition to the fumarate derivative of the present invention (I) or (II).

Examples of the radical polymerizable compound include unsaturated polyester, oligomer having (meth)acrylate group, and radical polymerizable monomer.

The unsaturated polyester is obtained by a polycondensation reaction of an α,β-unsaturated polybasic acid or an acid anhydride with a saturated polybasic acid and a polyhydric alcohol.

Examples of the α,β-unsaturated polybasic acid include maleic acid, fumaric acid, itaconic acid, maleic anhydride and itaconic anhydride. Examples of the saturated polybasic acid used in combination as an acid component include saturated aliphatic dicarboxylic acids such as succinic acid, adipic acid and sebacic acid; aromatic polycarboxylic acids such as phthalic anhydride, isophthalic acid, terephthalic acid, trimellitic acid, pyromellitic anhydride and 2,6-naphthalene dicarboxylic acid; and alicyclic dicarboxylic acids such as endic anhydride, 1,2-cyclohexanedicarboxylic acid, hexahydrophthalic anhydride and 1,4-cyclohexanedicarboxylic acid. Examples of the polyhydric alcohol include aliphatic diols such as ethylene glycol, diethylene glycol, 1,2-propanediol, 1,3-propanediol, dipropylene glycol, 1,3-butanediol, 1,4-butanediol, neopentyl glycol, 2-methyl-1,3-propanediol, 3-methyl-1,5-pentanediol, 1,6-hexanediol, 1,6-nonanediol and 1,9-nonanediol; alicyclic diols such as 1,4-cyclohexanedimethanol, tricyclodecanedimethanol and hydrogenated bisphenol A; aromatic diols such as ethylene oxide or propylene oxide adducts of bisphenol A; and trihydric or greater polyhydric alcohols such as glycerol, trimethylolpropane, trimethylolethane, pentaerythritol, sorbitol and dipentaerythritol.

Other examples of the unsaturated polyester include those obtained by a transesterification reaction of the above-described saturated polybasic acid with a dialkyl ester of the unsaturated polybasic acid and the polyhydric alcohol. In this case, the alkyl group is usually a methyl group, an ethyl group, a propyl group or a butyl group.

The (meth)acrylate-base compound for use in the present invention is a compound having two or more (meth)acryloyl groups in the structure and specifically, can be obtained by a reaction of a urethane (meth)acrylate, a polyhydric alcohol, a polybasic acid or an anhydride thereof, and a (meth) acrylic acid.

Specific examples thereof include polyester(meth)acrylates, polyether(meth)acrylates obtained by reacting a polyhydric alcohol resulting from addition of ethylene oxide or propylene oxide to a hydroxyl group-containing compound with a (meth)acrylic acid, epoxy (meth)acrylates obtained by reacting an epoxy compound with a (meth)acrylic acid or a (meth)acrylate having a carboxyl group, polyfunctional (meth)acrylates such as ethylene glycol di(meth)acrylate, diethylene glycol di(meth)acrylate, neopentyl glycol di(meth)acrylate, glycerol di(meth)acrylate, trimethylolethane tri(meth)acrylate, trimethylolpropane tri(meth)acrylate, pentaerythritol tri(meth)acrylate, pentaerythritol tetra (meth)acrylate and dipentaerythritol hexa(meth)acrylate, and silicon (meth)acrylates having a siloxane group and a (meth)acryloyl group.

The urethane (meth)acrylate for use in the present invention is known and can be obtained by reacting a polyhydric alcohol, a polyisocyanate and a hydroxyethyl(meth)acrylate or hydroxypropyl(meth)acrylate. Examples of the polyhydric alcohol include those described above for the polyhydric alcohol of the unsaturated polyester. Examples of the polyisocyanate include toluene diisocyanate, 4,4'-diphenylmethane isocyanate, xylene diisocyanate, hexamethylene diisocyanate and isophorone diisocyanate.

Examples of the polybasic acid and the polyhydric alcohol used as starting materials of the polyester(meth)acrylate or polyether(meth)acrylate for use in the present invention include those described above with respect to the unsaturated polyester.

Known examples of the epoxy compound used as a starting material of the epoxy (meth)acrylate for use in the present invention include epoxy resin-base compounds such as glycidyl ether of bisphenols(e.g., bisphenol A, bisphenol S, bisphenol F) and novolak.

The radical polymerizable monomer for use in the present invention has a double bond as a polymerizable group. Specific examples thereof include monofunctional (meth) acrylates such as methyl(meth)acrylate, ethyl(meth)acrylate, butyl(meth)acrylate, 2-ethylhexyl(meth)acrylate, phenyl (meth)acrylate, benzyl(meth)acrylate and isobornyl(meth) acrylate; aromatic vinyl compounds such as styrene, α-styrene, methoxy styrene and divinylbenzene; vinyl esters of aliphatic carboxylic acid, such as vinyl acetate, vinyl propionate, vinyl butyrate, vinyl pivalate, vinyl stearate and vinyl caproate; alicyclic vinyl esters such as vinyl ester of cyclohexanecarboxylic acid; vinyl ester of aromatic acid such as vinyl benzoate and vinyl t-butyl benzoate; hydroxyalkyl vinyl esters such as hydroxyethyl vinyl ester, hydroxypropyl vinyl ester and hydroxybutyl vinyl ester; allyl compounds such as diallyl phthalate, diallyl isophthalate, diallyl terephthalate, diallyl maleate, diallyl fumarate, diallyl itaconate, triallyl trimellitate, triallyl cyanurate, triallyl isocyanurate, diallyl carbonate, diethylene glycol bisallyl carbonate, trimethylol propane diallyl ether and pentaerythritol triallyl ether; maleimides such as N-methylmaleimide, N-cyclohexylmaleimide, N-phenylmaleimide, N-laurylmaleimide, N-2-methylphenylmaleimide, N-2-chlorophenylmaleimide, N-2-methoxyphenylmaleimide, N,N-4,4 1-diphenylmethane bismaleimide; unsaturated dibasic acids and derivatives thereof, such as maleic acid, fumaric acid, maleic anhydride, dimethyl maleate, diethyl maleate, dimethyl fumarate, diethyl fumarate, dimethyl itaconate and diethyl itaconate; and the fumarate derivatives represented by formulae (17) and (18).

Particularly, when the fumarate derivative represented by formula (17) or (18) is used and blended, the polymerizable composition of the present invention (IV) is not prone to curing inhibition by oxygen and can have good surface curability. These radical polymerizable monomers can be used individually or in combination of two or more thereof.

The amount of the fumarate derivative of the present invention (I) or (II) used in the polymerizable composition of the present invention (IV) is from 1 to 99% by mass, preferably from 5 to 80% by mass, in the curable composition. In particular, when the amount used is 5% by mass or more, the polymerizable composition is scarcely affected by the curing inhibition due to oxygen and can be prevented from occurrence of surface stickiness.

The radical polymerization initiator which can be used for the polymerizable composition of the present invention (IV) may be any radical polymerization initiator as long as it can generate a radical, for example, by heat, ultraviolet ray, electron beam or radiation.

Examples of the radical polymerization initiator which can be used in the radical polymerization by heat include azo-base compounds such as 2,2'-azobisisobutyronitrile and 2,2'-azobisisovaleronitrile; ketone peroxides such as methyl ethyl ketone peroxide, methyl isobutyl ketone peroxide and cyclohexanone peroxide; diacyl peroxides such as benzoyl peroxide, decanoyl peroxide and lauroyl peroxide; dialkyl peroxides such as dicumyl peroxide, tert-butylcumyl peroxide and di-tert-butyl peroxide; peroxy ketals such as 1,1-bis (tert-butylperoxy)3,3,5-trimethyl cyclohexane, 1,1-di-tert-butylperoxy cyclohexane and 2,2-di(tert-butylperoxy) butane; alkylperoxy esters such as tert-butylperoxy pivalate, tert-butylperoxy-2-ethyl hexanoate, tert-butylperoxy isobutylate, di-tert-butylperoxy hexahydroterephthalate, di-tert-butylperoxy azelate, tert-butylperoxy-3,5,5-trimethyl hexanoate, tert-butylperoxy acetate, tert-butylperoxy benzoate, di-tert-butylperoxy trimethyladipate, tert-butylperoxy 2-ethylhexanoate and tert-hexylperoxy 2-ethylhexanoate; and percarbonates such as diisopropylperoxy dicarbonate, di-sec-butylperoxy dicarbonate and tert-butylperoxy isopropylcarbonate.

In the film formation such as coating by heat, it is also possible to cause self-crosslinking without using a radical polymerization initiator.

Examples of the radical polymerization initiator which can be used for the polymerization by ultraviolet ray or electron beam include acetophenone derivatives such as acetophenone, 2,2-dimethoxy-2-phenylacetophenone, diethoxyacetophenone, 1-hydroxy-cyclohexyl-phenyl ketone, 2-methyl-1-[4-(methylthio)phenyl]-2-morpholinopropanone-1, 2-benzyl-2-dimethylamino-1-(4-morpholinophenyl)-butanone-1 and 2-hydroxy-2-methyl-1-phenyl-propan-1one; benzophenone derivatives such as benzophenone, 4,4'-bis(di -methylamino)benzophenone, 4-trimethysilybenzophenone and 4-benzoyl-4'-methyl-diphenylsulfide; benzoin derivatives such as benzoin, benzoin ethyl ether, benzoin propyl ether, benzoin isobutyl ether and benzoin isopropyl ether; methyl phenyl glyoxylate; benzoin dimethyl ketal; and 2,4,6-trimethylbenzoyldiphenylphosphine oxide.

The amount of the polymerization initiator used is from 0.01 to 15% by mass, preferably from 0.1 to 10% by mass, based on the weight of the polymerizable composition of the present invention (IV).

In the case of polymerizing the polymerizable composition of the present invention, various additives may be added according to the use end. Examples of the additives which can be used in combination include ultraviolet absorbent, antioxidant, coloring agent, lubricant, antistatic agent and inorganic filler such as silica, alumina and aluminum hydroxide.

The polymerizable composition of the present invention (IV) can be cured by a curing method using ultraviolet ray, electron beam or heat, such as coating by means of roll coater or spin coater, cast formation or photoformation.

Depending on the curing method, when the viscosity of the polymerizable composition of the present invention must be lowered, a solvent may be used. Examples of the solvent, which can be used, include aromatic hydrocarbons such as toluene and xylene; acetic acid esters such as methyl acetate, ethyl acetate, propyl acetate and butyl acetate; ketones such as acetone, methyl ethyl ketone and methyl isobutyl ketone; ethers such as tetrahydrofuran and dioxane; and alcohols such as ethyl alcohol, (iso)propyl alcohol and butyl alcohol.

The present invention (V) is described below. The present invention (V) is a cured product obtained by curing the polymerizable composition of the present invention (IV).

The cured product of the present invention (V) can be used over a wide range in the field of curable resin, for example, coating materials such as wood coating, film coating, metal coating, plastic coating, inorganic coating, hard coating, optical fiber coating and gel coating agent; painting materials such as coating or printing ink; optical materials such as photoformation material, optical disk, spectacle lens and prism; adhesive; photoresist; sealant; and molding materials. The cured product of the present invention (V) is useful particularly as a coating material for forming a thin film, which is prone to inhibition by oxygen. The substrate subjected to the coating is not particularly limited. Specific examples thereof include metal, glass and plastic.

The resin obtained by curing the polymerizable composition of the present invention has a high crosslinking density and therefore, a cured product having a high surface hardness can be obtained In particular, a cured resin of the fumarate derivative having a tri-, tetra, penta- or hexa-hydric alcohol in the skeleton, represented by formula (10), has a surface hardness as high as 4H to 8H in terms of the pencil hardness (JIS K-5400) and therefore, can be optimally used in the field where abrasion resistance or scratch resistance is required.

EXAMPLES

The present invention is described in greater detail below by referring to the Examples, however, the present invention should not be construed as being limited to these Examples as long as the spirit of the present invention is observed.

In the measurements of various data, the following instruments were used.

Instruments Used $^1$H-NMR

Model of instrument used: JEOL EX-400 (400 MHz)

A sample was dissolved in chloroform deuteride and measured using tetramethylsilane as the internal standard substance, and a chemical shift was calculated.

FT-IR

Model of instrument used:

Spectrum GX manufactured by Perkin-Elmer

The measurement was performed by a liquid film method using KBr plate.

GPC

Model of instrument used:

pump: Shodex DS-4, UV detector: Waters 484,

RI detector: Shodex RI SE-61

Column used:

Shodex K-G+K-801 (in Example 1, K-802 was added)

Measuring conditions:

eluent: chloroform, flow rate: 1 ml/min., column temperature: 40° C., detection: UV 254 nm GC (Monomer Analysis)

Model of instrument used:

GC-14B (manufactured by Shimadzu Seisakusho)

Column used:

DB-23, 0.25 μ×30 m (manufactured by J & W)

Carrier gas: nitrogen, 1 ml/min.

Split ratio: 1:50

Septum purge: 10 ml/min.

Detector: FID

Injection temperature: 230° C.

Detector temperature: 230° C.

Temperature program:

40° C. (10 min.)→(10° C./min.)→200° C.

UV Irradiation Apparatus

Model of instrument used:

TOSCURE 401 (manufactured by Toshiba K.K.),

Light source: mercury lamp,

Irradiation intensity:

irradiation distance: 100 mm–70 mW/cm$^2$

Melting Point

Model of instrument used:

MP-500D (manufactured by Yanaco)

Refractive Index

Model of instrument used:

Abbé's refractometer IT (manufactured by Atago)

Refractive index ($n^D$) was measured with use of the above instrument using α-bromonaphthalene as a contacting liquid.

Temperature: 25° C.

Example 1

Into a 1 L-volume flask equipped with a distillation unit, 312 g of bis(2-allyloxyethyl) maleate, 135 g of ethylene oxide 2-mol adduct of bisphenol A, 0.4 g of dibutyltin oxide and 0.12 g of tetrakis[methylene-3-(3,5-di-tert-butyl-4-hydroxyphenyl)propionate]methane ("IRGANOX 1010", trade name, produced by Chiba Specialty Chemicals) as a polymerization inhibitor were charged. While gradually reducing the pressure inside of the reaction system, the mixture was heated at 160° C. and ethylene glycol monoallyl ether generated as a by-product was distilled off. Finally, the pressure was reduced to about 400 Pa and a nearly theoretical amount of ethylene glycol monoallyl ether was distilled off.

After cooling the reaction solution to a room temperature, 385 g of the product was taken out. $^1$H-NMR and IR of the product obtained were measured and this product was identified as a condensate of bis(2-allyloxyethyl) maleate with ethylene oxide 2-mol adduct of bisphenol A.

By the GC analysis, the product was found to contain 30.3% of bis(2-allyloxyethyl) maleate.

$^1$H-NMR δ(ppm): 7.13–7.11 (m, Ph), 6.81–6.78 (m, Ph), 6.29 (s, —OCOC$\underline{H}$=C$\underline{H}$COO—), 5.95–5.84 (m, CH$_2$=C$\underline{H}$—CH$_2$—), 5.31–5.25 (m, C$\underline{H}_2$=CH—CH$_2$—), 5.21–5.17 (m, C$\underline{H}_2$=CH—CH$_2$—), 4.52–3.64 (m, —O—CH$_2$—C$\underline{H}_2$—COO—, CH$_2$=CH—C$\underline{H}_2$—, —O—C$\underline{H}_2$—CH$_2$—COO—, Ph-O—C$\underline{H}_2$—C$\underline{H}_2$—OCO—C=C—), 1.63 (S, Ph-C(Me)$_2$-Ph), 1.62 (Ph-C(Me)$_2$-Ph). IR ν(CO)=1,733 cm$^{-1}$, ν(allyl C=C, maleate C=C)=1,647 cm$^{-1}$ 62.4 g of the mixture obtained, 60 ml of toluene, 60 ml of 1-propanol and 6.2 g of Ru—C supported in an amount of 5% by mass were charged and after purging with nitrogen, the temperature was elevated to 150° C. Subsequently, the mixture was stirred under heating at the same temperature for 10 hours. After cooling, the catalyst was separated by filtration from the reaction solution and the solvent was distilled off under reduced pressure from the filtrate, as a result, 59.2 g of a highly viscous yellow liquid was obtained. By NMR, the isomerization ratio from the double bond of maleic acid residue (δ=6.29 ppm) to the double bond of fumaric acid residue (δ=6.93 to 6.86 ppm) was 100%.

The area percentage in the chart of analysis results by GPC of the product obtained is shown in Table 1 with respect to the condensation degree n (the number of repeating units) of the product.

TABLE 1

| Condensation degree n | 1 | 2 | 3 | 4 | ≧5 |
|---|---|---|---|---|---|
| Composition (area %) | 30.3 | 29.0 | 23.1 | 13.0 | 4.6 |

Example 2

Into a 3 L-volume glass flask, 500 g of maleic anhydride, 573 g of ethylene glycol monoallyl ether and 0.05 g of hydroquinone monomethyl ether were charged. The mixture was stirred under heating at 50° C. for 24 hours in a nitrogen atmosphere. To the reactant obtained, 1 kg of 1,4-dioxane, 10 g of concentrated hydrochloric acid and 0.1 g of hydroquinone monomethyl ether were added and the mixture was stirred under heating at 100° C. for 1 hour. Thereafter, 1,4-dioxane was distilled off under reduced pressure and to the reactant, 1 kg of toluene and 1 kg of water were added and liquid-separated. Toluene was distilled off under reduced pressure from the organic layer, as a result, 1,020 g of a pale yellow liquid was obtained. From the analyses by NMR and FT-IR, the product was identified as mono-2-allyloxyethyl fumarate.

$^1$H-NMR δ(ppm): 10.44 (br.s, 1H, —COO$\underline{H}$), 7.30–6.83 (m, 2H, —OCOC$\underline{H}$=C$\underline{H}$COO—), 5.92–5.88 (m, 1H, CH$_2$=C$\underline{H}$—CH$_2$—), 5.32–5.21 (m, 2H, C$\underline{H}_2$=CH—CH$_2$—), 4.37 (br.s, 2H, —O—CH$_2$—C$\underline{H}_2$—COO—), 4.07 (br.s, 2H, CH$_2$=CH—C$\underline{H}_2$—), 3.73 (br.s, 2H, —O—C$\underline{H}_2$—CH$_2$—COO—). IR ν(OH)=3,300–2,500 cm$^1$, ν(CO)=1,727 cm$^{-1}$, ν(allyl C=C)=1,647 cm$^{-1}$ Example 3

Into a 500 ml-volume glass flask equipped with a stirring unit, a thermometer, a condenser and distilling receiver with stopcock, 154 g of mono-2-allyloxyethyl fumarate obtained in Example 2, 21.8 g of pentaerythritol, 200 ml of benzene and 0.25 g of p-toluenesulfonic acid were charged. The mixture was stirred under heating in an oil bath, the reaction temperature was elevated to 80° C. and the reaction was continued while distilling off the water generated as a by-product with the progress of the reaction. When the amount of water distilled off reached the theoretical amount, the reaction was finished and the reaction solution was cooled. This reaction solution was transferred to a separatory funnel, 300 ml of benzene was added thereto, and the separation was performed using an aqueous 10% sodium carbonate solution and water. Thereafter, the resulting solution was concentrated under reduced pressure to obtain 120 g of a product.

$^1$H-NMR, FT-IR, GC and GPC of the product were measured and this product was identified as a composition containing a condensate of pentaerythritol with mono-2-allyloxyethyl fumarate, and 43% (by GC) of bis(2-allyloxyethyl) fumarate monomer.

IR ν(CO)=1,727 cm$^{-1}$, ν(allyl C=C)=1,647 cm$^{-1}$

Example 4

Into a 500 ml-volume glass flask equipped with a stirring unit, a thermometer, a condenser and distilling receiver with stopcock, 152 g of mono-2-allyloxyethyl fumarate obtained in Example 2, 21.5 g of trimethylol propane, 200 ml of benzene and 0.25 g of p-toluenesulfonic acid were charged. The mixture was stirred under heating in an oil bath, the reaction temperature was elevated to 80° C., and the reaction was continued while distilling off the water generated as a by-product with the progress of the reaction. When the amount of water distilled off reached the theoretical amount, the reaction was finished and the reaction solution was cooled. This reaction solution was transferred to a separatory funnel, 300 ml of benzene was added thereto, and the separation was performed using an aqueous 10% sodium carbonate solution and water. Thereafter, the resulting solution was concentrated under reduced pressure to obtain 118 g of a product.

$^1$H-NMR, FT-IR, GC and GPC of the product were measured and this product was identified as a composition containing a condensate of trimethylol propane with mono-2-allyloxyethyl fumarate, and 30% (by GC) of bis(2-allyloxyethyl) fumarate monomer.

IR ν(CO)=1,727 cm$^{-1}$, ν(allyl C=C)=1,647 cm$^{-1}$

Example 5

Into a 3 L-volume glass flask, 500.7 g of mono-2-allyloxyethyl fumarate obtained in Example 2 and 1.8 kg of tetrahydrofurane (THF) were charged. The inside of the reaction system was purged with nitrogen and then 345.5 g of potassium carbonate was added. After the completion of heat generation, the mixture was stirred for 1 hour and the reaction solution was cooled with ice water. Separately, a THF solution was prepared by dissolving 524.3 g of p-toluenesulfonyl chloride in 200 g of THF. When the temperature of the reaction solution reached 10° C. or less, the prepared p-toluenesulfonyl chloride/THF solution was added thereto and stirred for 30 minutes. Thereafter, 70.9 g of pentaerythritol and 691.1 g of potassium carbonate were added and stirred. After the completion of heat generation, the ice water was removed and the reaction solution was returned to a room temperature and further stirred for 2 hours.

Then, the reaction solution was concentrated, the concentrate was transferred to a separatory funnel, 2 kg of ethyl acetate was added, and the separation washing was performed using an aqueous 10% sodium carbonate solution and water. Thereafter, the resulting solution was concentrated under reduced pressure to obtain 240 g of a product.

$^1$H-NMR, FT-IR and GPC of the product were measured and this product was identified as a condensate of pentaerythritol with mono-2-allyloxyethyl fumarate, represented by formula (21).

IR ν(CO)=1,727 cm$^{-1}$, ν(allyl C=C)=1,647 cm$^{-1}$

Formula (21)

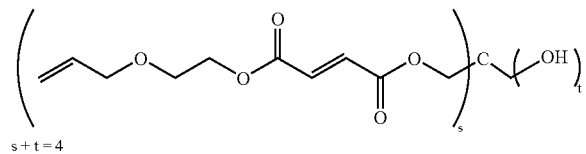

s+t=4

The area percentage in the chart of analysis results by GPC of the product obtained is shown in Table 2 with respect to the value of s in formula (21).

TABLE 2

| Value of s | 4 | 3 | 2≧ |
|---|---|---|---|
| Compositional ratio (area % by GPC) | 88.3 | 2.2 | 9.5 |

The mixture obtained above was subjected to thin layer chromatography ("Pre-coated TLC Plates SILICA GEL 60 F-254", produced by MERCK) in which silica was supported, using ethyl acetate/hexane=1/2 as the developer to isolate compounds having a value of s of 4 or 3. These compounds were measured by NMR and the above-described mixture was re-identified.

s=4

$^1$H-NMR δ(ppm) 6.92 (d, 4H, J=15.6 Hz, —OCOCH=CHCOO—), 6.85 (d, 4H, J=15.6 Hz, —OCOCH=CHCOO—), 5.96–5.86 (m, 4H, CH$_2$=CH—CH$_2$—), 5.30 (d, 4H, J=17.3 Hz, J=1.47 Hz, CH$_2$=CH—CH$_2$—), 5.22 (dd, 4H, J=10.5 Hz, J=1.47 Hz, CH$_2$=CH—CH$_2$—), 4.38 (t, 8H, J=4.6 Hz, —O—CH$_2$—CH$_2$—COO—), 4.34 (s, 8H, C—CH$_2$—), 4.04 (d, 8H, J=5.4 Hz, CH$_2$=CH—CH$_2$—), 3.70 (t, 8H, J=4.6 Hz, —O—CH$_2$—CH$_2$—COO—). IR ν(CO)=1,727 cm$^{-1}$, ν(allyl C=C)=1,647 cm$^{-1}$ s=3

$^1$H-NMR

δ(ppm) 6.92 (d, 3H, J=13.9 Hz, —OCOCH=CHCOO—), 6.87 (d, 3H, J=13.9 Hz, —OCOCH=CHCOO—), 5.96–5.86 (m, 3H, CH$_2$=CH—CH$_2$—), 5.30 (d, 3H, J=17.1 Hz, CH$_2$=CH—CH$_2$—), 5.22 (d, 3H, J=10.3 Hz, CH$_2$=CH—CH$_2$—), 4.38 (t, 6H, J=4.6 Hz, —O—CH$_2$—CH$_2$ COO—), 4.31 (s, 6H, C—CH$_2$—), 4.04 (d, 6H, J=5.9 Hz, CH$_2$=CH—CH$_2$—), 3.70 (t, 6H, J=4.6 Hz, —O—CH$_2$—CH$_2$—COO—) 3.63 (s, 2H, C—CH$_2$—). IR ν(CO)=1,727 cm$^{-1}$, ν(allyl C=C)=1,647 cm$^{-1}$ Example 6

Into a 3 L-volume glass flask, 500.2 g of mono-2-allyloxyethyl fumarate obtained in Example 2 and 1.8 kg of THF were charged. The inside of the reaction system was purged with nitrogen and then, 345.1 g of potassium carbonate was added. After the completion of heat generation, the mixture was stirred for 1 hour and the reaction solution was cooled with ice water. Separately, a THF solution was prepared by dissolving 524.3 g of p-toluenesulfonyl chloride in 200 g of THF. When the temperature of the reaction solution reached 10° C. or less, the p-toluenesulfonyl chloride/THF solution prepared was added and the reaction solution was stirred for 30 minutes. Thereafter, 93.2 g of trimethylolpropane and 691.0 g of potassium carbonate were added and stirred. After the completion of heat generation, the ice water was removed and the reaction solution was returned to a room temperature and further stirred for 2 hours.

Then, the reaction solution was concentrated, the concentrate was transferred to a separatory funnel, 2 kg of ethyl acetate was added, and the separation washing was performed using an aqueous 10% sodium carbonate solution and water. Thereafter, the resulting solution was concentrated under reduced pressure to obtain 267 g of a product. $^1$H-NMR, FT-IR and GPC of the product were measured and this product was identified as a condensate of trimethylolpropane with mono-2-allyloxyethyl fumarate, represented by formula (22).

IR ν(CO)=1,727 cm$^{-1}$, ν(allyl C=C)=1,647 cm$^{-1}$

Formula (22)

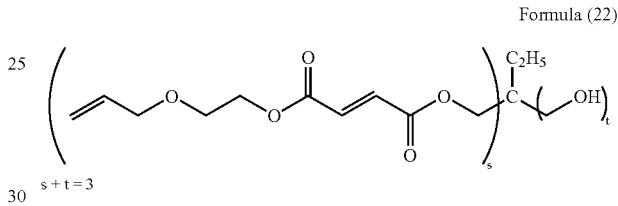

s+t=3

The area percentage in the chart of analysis results by GPC of the product obtained is shown in Table 3 with respect to the value of s in formula (22)

TABLE 3

| Value of s | 3 | 2≧ |
|---|---|---|
| Compositional ratio (area % by GPC) | 91.8 | 8.2 |

Example 7

Into a 1 L-volume round bottom flask equipped with a magnetic stirrer, a Dimroth condenser and a nitrogen inducing tube, 118.19 g of cyclohexanediol monoallyl ether, 148.71 g of maleic anhydride, 268 mg of hydroquinone monomethyl ether and 363 g of toluene were charged, and the mixture was stirred under heating at 110° C. for 24 hours in a nitrogen atmosphere. To the reactant obtained, 12.6 g of concentrated hydrochloric acid and 267 mg of hydroquinone monomethyl ether were added. The resulting mixture was heated under reflux for 5 hours in a nitrogen atmosphere and then cooled. The white precipitate deposited was separated by filtration through a 0.1 μm membrane filter and the filtrate was separated with water (500 ml×3 times). The obtained organic layer was dried over anhydrous magnesium sulfate and concentrated under reduced pressure by an evaporator, as a result, 162.49 g of a pale yellow viscous liquid was obtained. $^1$H-NMR and FT-IR of the product were measured and this product was identified as a mono-2-allyloxycyclohexyl fumarate.

IR ν(COOH)=3,300 cm$^{-1}$–2,500 cm$^{-1}$, ν(CO)=1,723 cm$^{-1}$, ν(allyl C=C)=1,646 cm$^{-1}$

Example 8

Into a 1 L-volume glass flask equipped with a stirring unit, a thermometer, a condenser and distilling receiver with stopcock, 161.53 g of mono-2-allyloxycyclohexyl fumarate obtained in Example 7, 103.37 g of cyclohexanediol monoallyl ether, 262.37 g of toluene, 8.6 g of p-toluenesulfonic acid and 520 mg of tetrakis[methylene-3-(3,5-di-tert-butyl-4-hydroxyphenyl)propionate]methane ("IRGANOX 1010", trade name, produced by Chiba Specialty Chemicals) as a polymerization inhibitor were charged. The mixture was refluxed under heating in an oil bath, and the reaction was continued while distilling off the water generated as a by-product with the progress of the reaction. When the amount of water distilled off reached the theoretical amount, the reaction was finished and the reaction solution was cooled. This reaction solution was transferred to a separatory funnel, 300 ml of toluene was added thereto, and the separation was performed using an aqueous 1N sodium hydroxide solution and water. Thereafter, the resulting solution was dried over sodium sulfate and concentrated under reduced pressure to obtain 230.28 g of a product. Thus obtained crude product was purified with a column chromatography as shown below.

130 g of silica gel (WAKO-GEL C-200, trade name, produced by Wako Jyunyaku Kogyo K. K.) in hexane slurry was filled in a chromato-column of 5 cm in diameter. 20.2 g of the crude product obtained above was charged in the chromato-column and eluted using ethyl acetate/hexane=1/10 as a developer to collect a fraction having an Rf value of 0.52 of the thin layer chromatography ("Pre-coated TLC Plates SILICA GEL 60 F-254", produced by MERCK). Thereafter, this fraction was concentrated under reduced pressure by an evaporator, as a result, 15.1 g of a pale yellow oily liquid was obtained. $^1$H-NMR, FT-IR and GPC of the product were measured and this product was identified as a bis(2-allyloxycyclohexyl) fumarate.

IR $\nu$(CO)=1,721 cm$^{-1}$, $\nu$(allyl C=C)=1,647 cm$^{-1}$

Example 9

Into a 500 ml-volume glass flask equipped with a stirring unit, a thermometer, a condenser and distilling receiver with stopcock, 53.9 g of mono-2-allyloxycyclohexyl fumarate obtained in Example 7, 6.0 g of pentaerythritol, 50 ml of toluene, 811.8 mg of p-toluenesulfonic acid and 54.6 mg of hydroquinone monomethyl ether were charged. The mixture was refluxed under heating in an oil bath, and the reaction was continued while distilling off the water generated as a by-product with the progress of the reaction. When the amount of water distilled off reached the theoretical amount, the reaction was finished and the reaction solution was cooled. This reaction solution was transferred to a separatory funnel, 300 ml of ethyl acetate was added thereto, and the separation was performed using an aqueous 10% sodium carbonate solution and water. Thereafter, the resulting solution was dried over sodium sulfate and concentrated under reduced pressure to obtain 38.9 g of a product.

$^1$H-NMR, FT-IR, GC and GPC of the product were measured and this product was identified as a composition containing a condensate of pentaerythritol with mono-2-allyloxycyclohexyl fumarate, and 40% (by GC) of bis(2-allyloxycyclohexyl) fumarate monomer.

IR $\nu$(CO)=1,723 cm$^{-1}$, $\nu$(allyl C=C)=1,645 cm$^{-1}$

Example 10

Into a 3 L-volume glass flask equipped with a stirring unit, 60.8 g of mono-2-allyloxycyclohexyl fumarate obtained in Example 7 and 200 ml of THF were charged. The inside of the reaction system was purged with nitrogen and then 22 g of potassium carbonate was added. After the completion of heat generation, the mixture was stirred for 1 hour and the reaction solution was cooled with ice water. When the temperature of the reaction solution reached 10° C. or less, 7.6 g of p-toluenesulfonyl chloride was added and stirred for 30 minutes. Thereafter, 5.4 g of pentaerythritol was added and stirred. The reaction solution was returned to a room temperature and stirred for 12 hours. Then, the reaction solution was concentrated, the concentrate was transferred to a separatory funnel, 500 ml of ethyl acetate was added, and the separation washing was performed using an aqueous 10% sodium carbonate solution and water.

Thereafter, the resulting solution was concentrated under reduced pressure to obtain 30 g of a product. $^1$H-NMR, FT-IR and GPC of the product were measured and the product was identified as a condensate of pentaerythritol with mono-2-allyloxycyclohexyl fumarate, represented by formula (23).

IR $\nu$(CO)=1,723 cm$^{-1}$, $\nu$(allyl C=C)=1,645 cm$^{-1}$

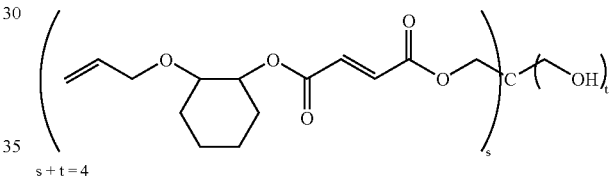

Formula (23)

$s+t=4$

The area percentage in the chart of analysis results by GPC of the product obtained is shown in Table 4 with respect to the value of s in formula (23).

TABLE 4

| Value of s | 4 | 3 | 2≧ |
|---|---|---|---|
| Compositional ratio (area % by GPC) | 82.2 | 2.0 | 15.8 |

Example 11

Into a 3 L-volume glass flask equipped with a dropping funnel, 1,400 g of allyl alcohol and 351.6 g of alumina (Alumina N Super I, trade name, produced by ICN) were charged. Also 500 g of styrene oxide was added through the dropping funnel while stirring under heating at 50° C. in a nitrogen atmosphere. After the completion of the addition, heating and stirring were continued for 10 hours. After cooling, the alumina was separated by filtration through a 0.1 μm membrane filter and the excess allyl alcohol was evaporated under reduced pressure from the reaction solution by an evaporator. Thereafter, the concentrated solution was distilled under reduced pressure to obtain 592 g (yield: 80%) of a mixture of 2-allyloxy-1-phenyl ethanol and 2-allyloxy-2-phenyl ethanol.

IR $\nu$(OH)=3,443 cm$^{-1}$, $\nu$(Ph, CH)=3,050 cm$^{-1}$–3,030 cm$^{-1}$, $\nu$(allyl C=C)=1,647 cm$^{-1}$ b.p.=136° C. (13 Torr)

Example 12

Into a 2 L-volume round bottom flask equipped with a induced magnetic stirrer, a Dimroth condenser and a nitrogen inducing tube, 322.9 g of 2-allyloxyphenyl ethanol obtained in Example 11, 354.9 g of maleic anhydride, 1.36 g of hydroquinone monomethyl ether and 677.5 g of toluene were charged, and the mixture was stirred under heating at 130° C. in an oil bath for 5 hours in a nitrogen atmosphere. After cooling, 80 g of concentrated hydrochloric acid was added to the reactant obtained. The resulting mixture was stirred under heating at 130° C. in an oil bath for 10 hours in a nitrogen atmosphere and then cooled. The precipitated fumaric acid was separated by filtration and the filtrate was separated with water. The obtained organic layer was dried over anhydrous sodium sulfate and toluene was evaporated under reduced pressure by an evaporator. Thereafter, the reaction solution was introduced into hexane to precipitate a white solid. Then the white solid was separated by filtration and dried under reduced pressure to obtain 375.8 g (yield: 75.1%) of mono(2-allyloxy-phenylethyl) fumarate. The thus obtained white solid was used in the next process without further purification.

IR $\nu(COOH)=3{,}400$ cm$^{-1}$–2,560 cm$^{-1}$, $\nu(CO)=1{,}723$ cm$^{-1}$, $\nu(\text{allyl C}=C)=1{,}645$ cm$^{-1}$ m.p.=71.2–71.4° C.

Example 13

Into a 500 ml-volume glass flask equipped with a stirring unit, a thermometer, a condenser and distilling receiver with stopcock, 138.14 g of mono(2-allyloxy-phenylethyl) fumarate obtained in Example 12, 89.125 g of 2-allyloxyphenyl ethanol, 150 ml of benzene, 2.76 g of p-toluensulfonic acid and 138 mg of hydroquinone monomethyl ether as a polymerization inhibitor were charged. The mixture was refluxed under heating in an oil bath, and the reaction was continued while distilling off the water generated as a by-product with the progress of the reaction. When the amount of water distilled off reached the theoretical amount, the reaction was finished and the reaction solution was cooled. This reaction solution was transferred to a separatory funnel, 300 ml of benzene was added thereto, and the separation was performed using an aqueous 1% sodium hydroxide solution and water. Thereafter, the resulting solution was dried over sodium sulfate and concentrated under reduced pressure to obtain 200 g of a crude product. Thus obtained crude product was purified by re-crystallization in hot hexane to obtain a white solid. $^1$H-NMR, FT-IR and GPC of the thus obtained white solid were measured and this solid was identified as a bis(2-allyloxy-phenylethyl) fumarate.

IR $\nu(Ph, CH)=3{,}050$ cm$^{-1}$–3,030 cm$^{-1}$, $\nu(CO)=1{,}725$ cm$^{-1}$, $\nu(\text{allyl C}=C)=1{,}647$ cm$^{-1}$ m.p.=68.3–68.5° C.

Example 14

Into a 1 L-volume glass flask, 75.7 g of mono(2-allyloxy-phenylethyl) fumarate obtained in Example 12 and 355.6 g of THF were charged. The inside of the reaction system was purged with nitrogen and then, 38 g of potassium carbonate was added. After the completion of heat generation, the mixture was stirred for 1 hour and the reaction solution was cooled with ice water. Separately, a THF solution was prepared by dissolving 51.5 g of p-toluenesulfonyl chloride in 89 g of THF. When the temperature of the reaction solution reached 10° C. or less, the p-toluenesulfonyl chloride/THF solution prepared was added and the reaction solution was stirred for 30 minutes. Thereafter, 7.5 g of pentaerythritol and 82.2 g of potassium carbonate were added and stirred. After the completion of heat generation, the ice water was removed and the reaction solution was returned to a room temperature and further stirred for 5 hours.

Then, the reaction solution was concentrated, the concentrate was transferred to a separatory funnel, 1 kg of ethyl acetate was added, and the separation washing was performed using an aqueous 10% sodium carbonate solution and water. Thereafter, the organic layer was concentrated under reduced pressure to obtain 32.5 g of a crude product. The thus obtained crude product was purified with a column chromatography as shown below.

1 kg of silica gel (WAKO-GEL C-200, trade name, produced by Wako Jyunyaku Kogyo K. K.) in hexane slurry was filled in a chromato-column of 10 cm in diameter. The crude product obtained above was charged in the chromato-column and eluted using ethyl acetate/hexane as a developer. By changing a ratio of the developer gradually from 1/20 to 1/5 to collect a fraction having an Rf value of 0.50 (developer: ethyl acetate/hexane=1/2) of the thin layer chromatography ("Pre-coated TLC Plates SILICA GEL 60 F-254", produced by MERCK). Thereafter, this fraction was concentrated under reduced pressure by an evaporator, as a result, 10.1 g of a pale yellow oily liquid was obtained. $^1$H-NMR, FT-IR and GPC of the product were measured and this product was identified as a condensate of pentaerythritol with mono(2-allyloxy-phenylethyl) fumarate, represented by formula (24) and value of s is 4.

IR $\nu(Ph, CH)=3{,}080$ cm$^{-1}$–3,030 cm$^{-1}$, $\nu(CO)=1{,}725$ cm$^{-1}$, $\nu(\text{allyl C}=C)=1{,}647$ cm$^{-1}$

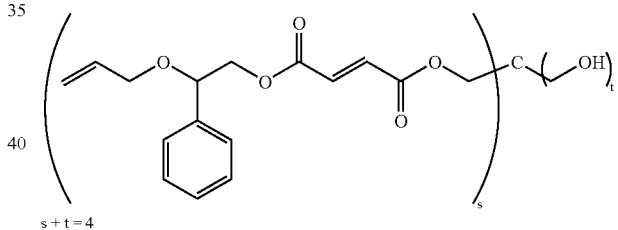

Formula (24)

Example 45

Into a 300 ml-volume glass flask equipped with a condenser, 20.0 g of fumaric acid, 37.22 g of cyclohexene oxide, 60.8 g of 1,4-dioxane and 3.7 g of alumina (Alumina N-Super I, trade name, produced by ICN Pharmaceuticals) were charged. After purging the reaction system with nitrogen, heating and stirring were continued at 60° C. for 13.5 hours. Filtrating the resultant reaction solution through membrane filter and distilling off the filtrate under reduced pressure gave 40.7 g of transparent oily liquid.

Successively, into a 100 ml-volume glass flask equipped with a stirring unit, a thermometer, a condenser and distilling receiver with stopcock, 10.3 g of transparent oily liquid obtained above, 17 g of mono-2-allyloxycyclohexyl fumarate obtained in Example 7, 26.7 g of toluene, 338.2 mg of p-toluenesulfonic acid and 10 mg of hydroquinone monomethyl ether as a polymerization inhibitor were charged. The mixture was heated under reflux in an oil bath, and the reaction was continued while distilling off water generated as a by-product with the progress of the reaction. When the amount of water distilled off reached the theoretical amount, the reaction was finished and the reaction solution was cooled. Toluene was distilled off under reduced pressure from the reaction solution to obtain a viscous yellow liquid. And after a small amount of ethyl acetate was added thereto, it was re-precipitated by introducing in hexane. Thus obtained white viscous solid was washed with water and further with hexane to obtain 15 g of white solid. $^1$H-NMR, FT-IR and GPC of the thus obtained white solid were measured and this solid was identified as a polycondensate of 1,2-cyclohexanediol with fumaric acid and allyl alcohol.

IR $\nu$(CO)=1,722 cm$^{-1}$, $\nu$(allyl C=C)=1,647 cm$^{-1}$

Examples 15~20

50 g of the mixture obtained in Example 3, 50 g of toluene, 10 mg of hydroquinone monomethyl ether (MEHQ) and 15 g of 5% Pd—Al$_2$O$_3$ were added and after purging the inside of the reaction system with nitrogen, the mixture was stirred under heating at 140° C. for 3 hours. After cooling, 5% Pd—Al$_2$O$_3$ was removed by filtration from the reaction solution and then toluene was distilled off under reduced pressure from the filtrate to obtain 48 g of a pale yellow viscous liquid. $^1$H-NMR was measured and by comparing the peaks of ally group and propenyl group, it was confirmed that 98% was isomerized into propenyl group.

The isomerization reaction of the mixtures obtained in Examples 4, 5, 6, 7 and 8 was performed by the same operation. The results are shown together in Table 5.

TABLE 5

| | Charging | | | | |
|---|---|---|---|---|---|
| Example | Example where Starting Material used for Reaction is described | Starting Material (g) | Toluene (g) | Catalyst (g) | MEHQ (mg) | Reaction Results Isomerization ratio (%) |
| 15 | 3 | 50 | 50 | 15 | 10 | 98 |
| 16 | 4 | 50 | 50 | 15 | 10 | 100 |
| 17 | 5 | 85 | 85 | 25 | 18 | 100 |
| 18 | 6 | 50 | 50 | 15 | 10 | 98 |
| 19 | 7 | 50 | 50 | 15 | 10 | 98 |
| 20 | 8 | 50 | 50 | 15 | 10 | 99 |

Example 21

34 g of the crude product obtained in Example 14, 90 g of toluene, 10 mg of hydroquinone monomethyl ether (MEHQ) and 3.13 g of carbonylchlorohydridetris(triphenylphosphine) ruthenium(II) were added and after purging the inside of the reaction system with nitrogen, the mixture was stirred under heating at 140° C. for 3 hours. After cooling, toluene was distilled off under reduced pressure from the reaction solution to obtain 33 g of a pale yellow viscous liquid. $^1$H-NMR was measured and by comparing the peaks of ally group and propenyl group, it was confirmed that 98% was isomerized into propenyl group.

Examples 22 to 35

The fumarate derivatives of the present invention obtained in the Examples above each was coated on a glass substrate and cured by UV or heat. The surface hardness of the cured film was examined. The surface hardness was determined in accordance with the pencil scratch test of JIS K 5400.

The results are shown in Table 6.

TABLE 6

| | | Curing Conditions | | | |
|---|---|---|---|---|---|
| Example | Fumarate Derivative | Curing Method | Initiator | Temperature–Time/UV Exposure | Pencil Hardness |
| 22 | Compound of Example 1 | heat | none | 150° C. – 1 h | 5 H |
| 23 | Compound of Example 3 | heat | none | 150° C. – 1 h | 6 H |
| 24 | Compound of Example 4 | heat | DCP[1] 2% | 150° C. – 0.5 h | 6 H |
| 25 | Compound of Example 5 | heat | DCP[1] 2% | 150° C. – 0.5 h | 7 H |
| 26 | Compound of Example 6 | UV | IRG184[2] 5% | 900 mj/cm$^2$ | 6 H |
| 27 | Compound of Example 8 | heat | none | 150° C. – 1 h | 7 H |
| 28 | Compound of Example 9 | UV | IRG184[2] 5% | 300 mj/cm$^2$ | 7 H |
| 29 | Compound of Example 10 | UV | IRG184[2] 5% | 300 mj/cm$^2$ | 6 H |
| 30 | Compound of Example 14 | heat | none | 150° C. – 1 h | 6 H |
| 31 | Compound of Example 17 | UV | IRG184[2] 5% | 300 mj/cm$^2$ | 7 H |

TABLE 6-continued

| | | Curing Conditions | | | |
|---|---|---|---|---|---|
| Example | Fumarate Derivative | Curing Method | Initiator | Temperature–Time/UV Exposure | Pencil Hardness |
| 32 | Compound of Example 17 | heat | none | 150° C. – 1 h | 8 H |
| 33 | Compound of Example 18 | heat | none | 150° C. – 1 h | 7 H |
| 34 | Compound of Example 20 | UV | IRG184[2] 5% | 300 mj/cm$^2$ | 7 H |
| 35 | Compound of Example 21 | heat | none | 150° C. – 1 h | 6 H |
| Comparative Example 1 | Compound of Comparative Example 1 | UV | IRG184[2] 5% | 1200 mj/cm$^2$ | HB |

TABLE 6-continued

|  | | Curing Conditions | | | |
| --- | --- | --- | --- | --- | --- |
| Example | Fumarate Derivative | Curing Method | Initiator | Temperature–Time/UV Exposure | Pencil Hardness |
| Comparative Example 2 | Compound of Comparative Example 2 | heat | DCP[1] 2% | 150° C. – 1 h | 2 H |

[1]DCP: Dicumyl Peroxide
[2]IRG184: IRGACURE184, 1-Hydroxy-Cyclohexyl-phenyl-keton, trade name, produced by Chiba Specialty Chemicals Comparative Example 1

Into a 1 L-volume flask equipped with a distillation unit, 144 g of dimethyl fumarate, 245 g of ethylene glycol monoallyl ether, 0.2 g of dibutyltin oxide were charged. The mixture was heated at 140° C. in a nitrogen atmosphere and methanol generated as a by-product was distilled off. When methanol reached 70% of the theoretical amount, the pressure inside of the reaction system was gradually reduced to accelerate the distillation of methanol, and by finally reducing the pressure to about 400 Pa, the theoretical amount of methanol and the residual ethylene glycol monoallyl ether were completely distilled off. The reaction solution was cooled to a room temperature and then 283 g of a product was taken out. $^1$H-NMR and FT-IR of the product obtained were measured and this product was identified as bis(2-allyloxyethyl) fumarate.

This product was coated on a glass substrate and cured by UV. The surface hardness of the cured film was examined. The surface hardness was determined in accordance with the pencil scratch test of JIS K 5400.

The results are shown in Table 6 above.

Comparative Example 2

Into a 1 L-volume flask equipped with a distillation unit, 144 g of dimethyl fumarate, 279 g of hydroxybutyl vinyl ether, 0.2 g of zinc acetate and 0.3 g of IRGANOX 1010 as a polymerization inhibitor were charged. The mixture was heated to 140° C. in a nitrogen atmosphere and methanol generated as a by-product was distilled off. When methanol reached 70% of the theoretical amount, the pressure inside of the reaction system was gradually reduced to accelerate the distillation of methanol, and by finally reducing the pressure to about 400 Pa, the theoretical amount of methanol and the residual hydroxybutyl vinyl ether were completely distilled off. The reaction solution was cooled to a room temperature and then 297 g of bis(4-vinyloxybutyl) fumarate was obtained.

This product was coated on a glass substrate and cured by heat. The surface hardness of the cured film was examined. The surface hardness was determined in accordance with the pencil scratch test of JIS K 5400.

The results are shown in Table 6 above.

Examples 36 to 42, 46 and Comparable Examples 3 to 4

A composition of the fumarate derivative of the present invention was coated on a PET film or a glass substrate and cured by UV or heat. The surface hardness of the cured film was examined. The tack-free coating having no tackiness on the cured surface was rated ○ and the coating having tackiness was rated X.

The curing was performed under the following conditions.
(i) Heat curing
  Temperature 150° C.-1 hour
(ii) UV curing
  Initiator: IRGACURE-184, 5%
  Exposure: 300 mj/cm$^2$ The results are shown in Table 7 blow.

TABLE 7

|  |  | Example 36 | Example 37 | Example 38 | Example 39 | Example 40 | Example 41 | Example 42 | Example 46 | Comparative Example 3 | Comparative Example 4 |
| --- | --- | --- | --- | --- | --- | --- | --- | --- | --- | --- | --- |
| Blending, % by weight | Compound of Example 1 | 70 | | | | | | | | | |
|  | Compound of Example 10 | | 50 | | | | | | | | |
|  | Compound of Example 15 | | | | | | | | 70 | | |
|  | Compound of Example 17 | | | 50 | 80 | 50 | | 60 | | | |
|  | Compound of Example 18 | | | | | | 80 | | | | |
|  | PE-TA[3] | | | 50 | | | | | | 100 | |
|  | 80MFA[4] | | | | 20 | | | | | | 100 |
|  | 8524[5] | | | | | | 20 | 20 | | | |
|  | BPF[6] | 30 | 50 | | | 50 | | 20 | 30 | | |
| Curing Method |  | (i) | (i) | (i) | (i) | (ii) | (ii) | (ii) | (i) | (i) | (ii) |
| Film Properties | Tack | ○ | ○ | ○ | ○ | ○ | ○ | ○ | ○ | X | ○ |
|  | Pencil hardness | 5 H | 6 H | 7 H | 6 H | 2 H | 2 H | 2 H | 5 H | — | F |
| Substrate |  | glass | glass | glass | glass | PET | PET | PET | glass | glass | PET |

[3]PE-TA: pentaerythrytol triacrylate,
[4]Epoxy Ester 80MFA: epoxy acrylate, trade name, produced by Kyoei-Sha Kagaku.
[5]Unsaturated Polyester 8524: trade name, produced by Japan U-PICA Co. Ltd.
[6]BPF: bis[2-(1-propenyloxy) ethyl fumarate]

Example 43

After bis(2-allyloxy-phenylethyl) fumarate as described in Example 13 was melted at 80° C., 2% by mass of 1,1-bis(tert-hexylperoxy)3,3,5-trimethyl cyclohexane as a radical polymerization initiator was added thereto and the polymerizable composition was cured by casting at a temperature of 110° C. (1 hour), successively at 130° C. (1 hour) The refractive index of the obtained cured product was measured, and $n_D$ was 1.5573.

Example 44

1% by mass of tert-hexylperoxy 2-ethylhexanoate as a radical polymerization initiator was added to the condensate of pentaerythritol with mono(2-allyloxy-phenylethyl) fumarate as described in Example 14, and the polymerizable composition was cured by casting at a temperature of 80° C. (1 hour), successively at 120° C. (1 hour). The refractive index of the obtained cured product was measured, and $n_D$ was 1.5520.

Comparative Example 5

2% by mass of 1,1-bis(tert-hexylperoxy)3,3,5-trimethyl cyclohexane as a radical polymerization initiator was added to bis(2-allyloxyethyl) fumarate as described in Comparative Example 1, and casting cured the polymerizable composition. The refractive index of the obtained cured product was measured, and $n_D$ was 1.5132.

Effects of the Invention

As described in the foregoing pages, the fumarate derivative of the present invention has the terminal alkenyloxy group which copolymerizability is high as compared with conventional fumarate derivatives, so that the crosslinking degree can increase and a cured product having excellent surface hardness can be e n -provided. Also, the composition thereof with other polymerizable compounds can be used similarly for the purpose of improving the curability and the surface hardness. Moreover, a cured product made of the fumarate derivative containing an aryl group of the present invention has high refractive index of equal to or more than 1.55. Therefore, the cured product of the present invention is expected to apply for use of high refractive index.

The invention claimed is:

1. The fumarate derivative, which is represented by formula (10):

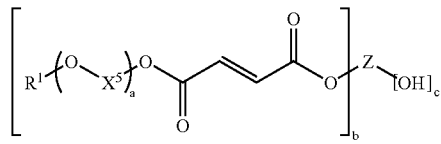

Formula (10)

(wherein Z represents an organic residue derived from a tri-, tetra-, penta- or hexa-hydric alcohol, $R^1$ independently represents formula (3) or formula (4), each $X^5$, which is present in the number of a in formula (10), independently represents an alkylene group or a cycloalkylene group having from 5 to 12 carbon atoms, a represents an integer of 1 to 5, b represents an integer of 1 to 6, c represents an integer of 0 to 5, and b+c is from 3 to 6);

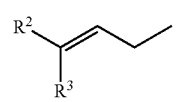

Formula (3)

(wherein $R^2$ and $R^3$ each independently represents hydrogen atom or an alkyl group having from 1 to 5 carbon atoms);

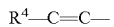

Formula (4)

(wherein $R^4$ represents hydrogen atom or an alkyl group having from 1 to 11 carbon atoms).

2. The fumarate derivative as claimed in claim 1, wherein $X^5$ in formula (10) is an alkylene group represented in formula (6):

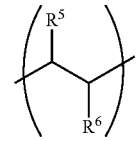

Formula (6)

(wherein $R^5$ and $R^6$ each independently represents hydrogen atom or formula (7));

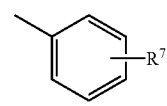

Formula (7)

(wherein $R^7$ represents hydrogen atom or an alkyl group having from 1 to 3 carbon atoms).

3. A polymerizable composition comprising the fumarate derivative as claimed in claim 1 or 2.

* * * * *